(12) United States Patent
Shmayahu et al.

(10) Patent No.: US 12,733,984 B2
(45) **Date of Patent: *Sep. 15, 2026**

(54) MULTI-ARM ROBOTIC SYSTEM FOR SPINE SURGERY WITH IMAGING GUIDANCE

(71) Applicant: Mazor Robotics Ltd., Caesarea (IL)

(72) Inventors: Yizhaq Shmayahu, Ramat HaSharon (IL); Eliyahu Zehavi, Tel-Aviv (IL); Yonatan Ushpizin, Glil Yam (IL); Noam Weiss, Haifa (IL)

(73) Assignee: Mazor Robotics Ltd., Caesarea (IL)

( * ) Notice: Subject to any disclaimer, the term of this patent is extended or adjusted under 35 U.S.C. 154(b) by 22 days.

This patent is subject to a terminal disclaimer.

(21) Appl. No.: 18/976,822

(22) Filed: Dec. 11, 2024

(65) Prior Publication Data

US 2025/0107852 A1 Apr. 3, 2025

Related U.S. Application Data

(63) Continuation of application No. 17/130,516, filed on Dec. 22, 2020, now Pat. No. 12,193,750.

(Continued)

(51) Int. Cl.

*A61B 34/30* (2016.01)
*A61B 34/10* (2016.01)

(Continued)

(52) U.S. Cl.

CPC .............. *A61B 34/10* (2016.02); *A61B 34/20* (2016.02); *A61B 34/30* (2016.02); *B25J 9/1676* (2013.01);

(Continued)

(58) Field of Classification Search

CPC ......... A61B 34/10; A61B 34/20; A61B 34/30; A61B 2034/102; A61B 2034/105;

(Continued)

(56) References Cited

U.S. PATENT DOCUMENTS

| | | | |
|---|---|---|---|
| 8,108,072 | B2 | 1/2012 | Zhao et al. |
| 8,571,638 | B2 | 10/2013 | Shoham |

(Continued)

FOREIGN PATENT DOCUMENTS

| | | |
|---|---|---|
| CN | 1286438 | 11/2006 |
| CN | 104856720 | 8/2017 |

(Continued)

OTHER PUBLICATIONS

An et al. "An Ultrasound Imaging-Guided Robotic HIFU Ablation Experimental System and Accuracy Evaluations," Applied Bionics and Biomechanics, 2017, vol. 2017, Article ID 5868695, 9 pages.

(Continued)

*Primary Examiner* — Dylan M Katz

(74) *Attorney, Agent, or Firm* — Sheridan Ross PC

(57) ABSTRACT

Systems and methods for monitoring a surgical procedure are provided. A coordinate system of a first robotic arm and a second robotic arm may be co-registered or correlated to each other. One or more poses of an imaging device may be determined to provide real-time intraoperative imaging of a region of interest during a surgical procedure. Anatomical elements may be identified in the real-time images of the region of interest from which a surgical tool should maintain a predetermined distance. The surgical tool may be prevented from approaching the identified anatomical elements by less than a predetermined distance using the co-registration of the coordinate systems.

20 Claims, 7 Drawing Sheets

Related U.S. Application Data

(60) Provisional application No. 63/052,763, filed on Jul. 16, 2020, provisional application No. 63/052,766, filed on Jul. 16, 2020, provisional application No. 62/952,958, filed on Dec. 23, 2019.

(51) Int. Cl.
*A61B 34/20* (2016.01)
*B25J 9/16* (2006.01)
*G06N 20/00* (2019.01)

(52) U.S. Cl.
CPC ........ *G06N 20/00* (2019.01); *A61B 2034/102* (2016.02); *A61B 2034/105* (2016.02); *A61B 2034/107* (2016.02); *A61B 2034/303* (2016.02)

(58) Field of Classification Search
CPC ........ A61B 2034/107; A61B 2034/303; A61B 6/4441; A61B 8/12; A61B 2090/364; A61B 2090/367; A61B 34/32; A61B 90/03; A61B 90/361; B25J 9/1676; G06N 20/00; G06N 3/0464; G06N 3/09; G06N 3/08; G16H 20/40; G16H 40/63; G16H 30/40
See application file for complete search history.

(56) References Cited

U.S. PATENT DOCUMENTS

| | | | | |
|---|---|---|---|---|
| 8,663,130 | B2 | 3/2014 | Neubach et al. | |
| 9,420,995 | B2 | 8/2016 | Neubach et al. | |
| 9,984,437 | B2 | 5/2018 | Thienphrapa et al. | |
| 10,159,534 | B2 | 12/2018 | Maillet et al. | |
| 10,290,076 | B2 | 5/2019 | Kadoury et al. | |
| 10,335,116 | B2 | 7/2019 | Boctor et al. | |
| 10,349,917 | B2 | 7/2019 | Boctor et al. | |
| 10,383,765 | B2 | 8/2019 | Alvarez et al. | |
| 10,917,543 | B2 | 2/2021 | Ramirez et al. | |
| 12,193,750 | B2 * | 1/2025 | Shmayahu | A61B 90/03 |
| 2007/0021738 | A1 | 1/2007 | Hasser et al. | |
| 2008/0247506 | A1 | 10/2008 | Maschke | |
| 2012/0143084 | A1 | 6/2012 | Shoham | |
| 2013/0035583 | A1 | 2/2013 | Park et al. | |
| 2015/0366546 | A1 | 12/2015 | Kamen et al. | |
| 2016/0135816 | A1 | 5/2016 | Lavallee et al. | |
| 2016/0151120 | A1 | 6/2016 | Kostrzewski et al. | |
| 2016/0279799 | A1 | 9/2016 | King et al. | |
| 2017/0055940 | A1 | 3/2017 | Shoham | |
| 2018/0042680 | A1 | 2/2018 | Dimaio et al. | |
| 2018/0200002 | A1 | 7/2018 | Kostrzewski et al. | |
| 2018/0250087 | A1 | 9/2018 | Grasser et al. | |
| 2019/0069957 | A1 | 3/2019 | Barral et al. | |
| 2019/0125457 | A1 | 5/2019 | Parihar et al. | |
| 2020/0281667 | A1 | 9/2020 | Blondel et al. | |
| 2021/0030476 | A1 | 2/2021 | Nakashima et al. | |
| 2022/0313366 | A1 | 10/2022 | Finley et al. | |
| 2023/0255696 | A1 | 8/2023 | Roh et al. | |

FOREIGN PATENT DOCUMENTS

| | | |
|---|---|---|
| CN | 108882967 | 11/2018 |
| FR | 3073135 | 5/2019 |
| JP | 2015-505686 | 2/2015 |
| WO | WO 2018/094240 | 5/2018 |

OTHER PUBLICATIONS

Du et al. "Development of an AVF Stenosis Assessment Tool for Hemodialysis Patients Using Robotic Ultrasound System," Micromachines, 2018, vol. 9, No. 2, Article 51, 15 pages.
Maintz et al. "An Overview of Medical Image Registration Methods," 1998, 22 pages.
Oguro et al. "Image registration of pre-procedural MRI and intra-procedural CT images to aid CT-guided percutaneous cryoablation of renal tumors," International Journal of Computer Assisted Radiology and Surgery, Jan. 2011, vol. 6, No. 1, pp. 111-117.
Prabu et al. "Robotically Assisted Brain Tumor Surgical System," International Journal of Advanced Computing and Communication Systems (IJACCS), Nov. 2014, vol. 1, No. 3, 6 pages.
Swerdlow et al. "Robotic Arm-Assisted Sonography: Review of Technical Developments and Potential Clinical Applications," American Journal of Roentgenology, Apr. 2017, vol. 208, No. 4, pp. 733-738.
Stoianovici et al. "Endocavity Ultrasound Probe Manipulators," IEEE, IEEE/ASME Transactions on Mechatronics, Jun. 2013, vol. 18, No. 3, pp. 914-921.
International Search Report and Written Opinion for International (PCT) Patent Application No. PCT/IB2020/062330, dated Mar. 15, 2021 19 pages.
International Preliminary Report on Patentability for International (PCT) Patent Application No. PCT/IB2020/062330, dated Jul. 7, 2022 12 pages.
Official Action for U.S. Appl. No. 17/130,516, dated Sep. 12, 2023 26 pages.
Official Action for U.S. Appl. No. 17/130,516, dated Jan. 3, 2024 28 pages.
Official Action for U.S. Appl. No. 17/130,516, dated Apr. 12, 2024 32 pages.
Notice of Allowance for U.S. Appl. No. 17/130,516, dated Sep. 12, 2024 9 pages.
Extended Search Report for European Patent Application No. 25205276.6, dated May 8, 2026, 9 pages.
Official Action for European Patent Application No. 25205276.6, dated Jan. 15, 2026, 4 pages.

* cited by examiner

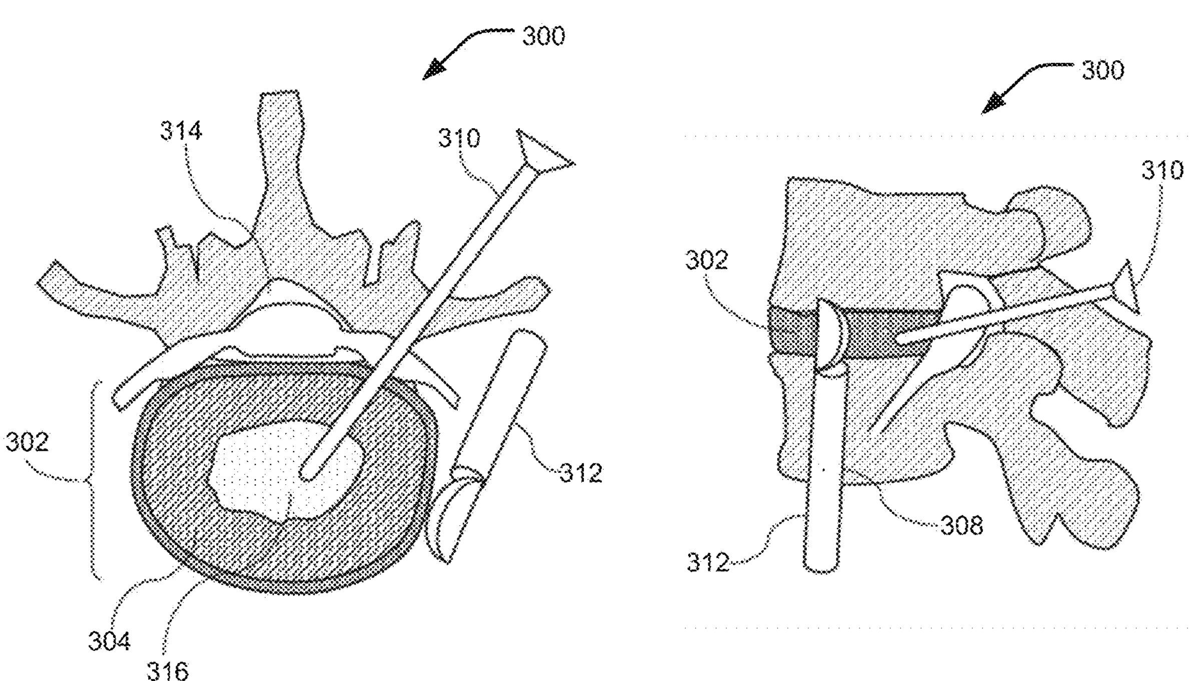
FIG. 3A
FIG. 3B
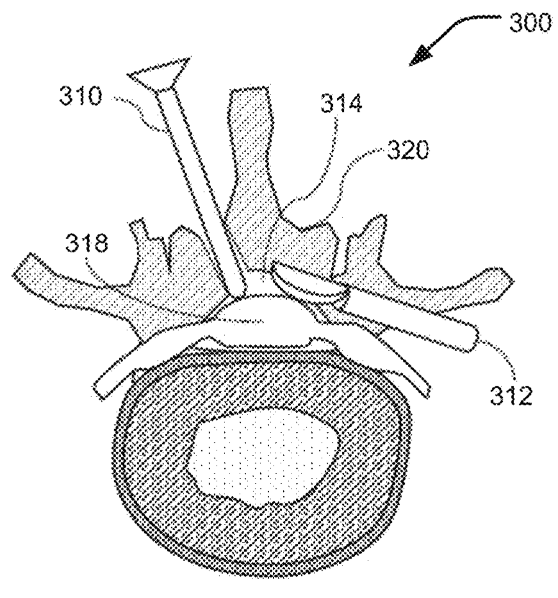
FIG. 3C
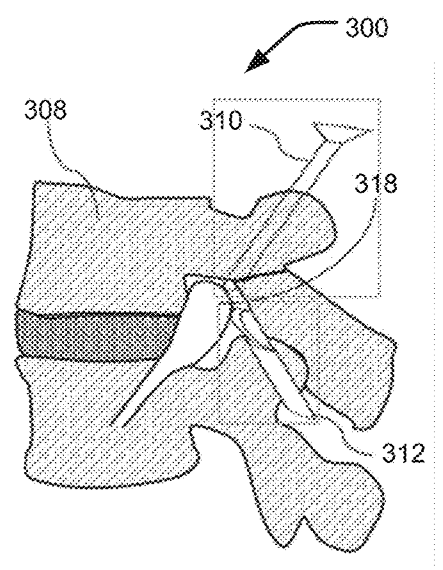
FIG. 3D

MULTI-ARM ROBOTIC SYSTEM FOR SPINE SURGERY WITH IMAGING GUIDANCE

CROSS REFERENCE TO RELATED APPLICATIONS

This application is a continuation of U.S. application Ser. No. 17/130,516, filed on Dec. 22, 2020, which claims the benefit of U.S. Provisional Application No. 62/952,958, filed on Dec. 23, 2019 and entitled "Multi-Arm Robotic System for Spine Surgery with Endoscopic Ultrasound Guidance"; U.S. Provisional Application No. 63/052,763, filed on Jul. 16, 2020 and entitled "System and Method for Image Generation Based on Calculated Robotic Arm Positions"; and U.S. Provisional Application No. 63/052,766, filed on Jul. 16, 2020 and entitled "System and Method for Image Generation Based on Calculated Robotic Arm Positions." Each of the foregoing applications is incorporated herein by reference in its entirety.

FIELD

Embodiments of the present disclosure relate to the field of imaging guidance in robotically performed spinal surgery, particularly in using automatic positioning of imaging device(s) and surgical tool(s).

BACKGROUND

During spine surgery, continuous and accurate information concerning the position of surgical tools and their effect on anatomical elements is valuable for guiding consequent surgical steps. Fluoroscopy is widely employed to provide intra-procedural imaging because it provides visualization of bony elements and metal tools and implants. Other forms of imaging are also used to provide visual guidance during a surgical procedure.

SUMMARY

Example aspects of the present disclosure include:

A robotic system according to at least one embodiment of the present disclosure comprises: a first robotic arm configured to orient an imaging device; a second robotic arm configured to orient at least one surgical tool; at least one processor; and at least one memory storing instructions for execution by the at least one processor that, when executed, cause the at least one processor to: correlate coordinate systems of the first robotic arm and the second robotic arm; analyze interoperative images obtained from the imaging device to identify anatomical elements for the surgical tool to avoid; and prevent the surgical tool from approaching the identified anatomical elements.

Any of the aspects herein, wherein identifying the anatomical elements is accomplished through image processing.

Any of the aspects herein, wherein identifying the anatomical elements is accomplished through machine learning recognition of images of anatomic elements from a database.

Any of the aspects herein, wherein the memory stores additional instructions for execution by the at least one processor that, when executed, further cause the at least one processor to: cause the second robotic arm to perform a surgical procedure using the at least one surgical tool.

Any of the aspects herein, wherein the imaging device is configured to acquire three-dimensional images by use of at least two imaging positions of the imaging device.

Any of the aspects herein, wherein the memory stores additional instructions for execution by the at least one processor that, when executed, further cause the at least one processor to: cause the first robotic arm to position the imaging device at each of the at least two imaging positions according to a surgical plan.

Any of the aspects herein, wherein the memory stores additional instructions for execution by the at least one processor that, when executed, further cause the at least one processor to: calculate a volume of an anatomical feature during the surgical procedure.

Any of the aspects herein, wherein the anatomical element undergoing the surgical procedure is an intervertebral disc.

Any of the aspects herein, wherein the surgical procedure comprises one of a vertebral discectomy, a laminectomy, a foraminotomy, or a laminotomy, the surgical procedure being carried out either transcutaneously or by open surgery.

Any of the aspects herein, wherein the memory stores additional instructions for execution by the at least one processor that, when executed, further cause the at least one processor to: cause the first robotic arm to reposition the imaging device if the region in which the surgical tool is operating becomes situated outside a field of view of the imaging device.

Any of the aspects herein, wherein the memory stores additional instructions for execution by the at least one processor that, when executed, further cause the at least one processor to: cause the first robotic arm to reposition the imaging device if any of the identified anatomical elements become situated outside a field of view of the imaging device.

Any of the aspects herein, wherein the identified anatomical element is one of a spinal nerve, a nerve root, a dorsal root ganglion, an intervertebral disc, a spinal meninges, a spinal cord, a vertebral foramen, or an intervertebral foramen.

Any of the aspects herein, wherein the memory stores additional instructions for execution by the at least one processor that, when executed, further cause the at least one processor to: provide instructions to position and operate the at least one surgical tool.

Any of the aspects herein, wherein the instructions comprise a plan for a surgical procedure based on one of a set of three-dimensional preoperative images or an intraoperative plan designed by a surgeon.

Any of the aspects herein, wherein the memory stores additional instructions for execution by the at least one processor that, when executed, further cause the at least one processor to: modify the preoperative plan to optimize the pose of the surgical tool based on images received from the imaging device.

A robotic system according to at least one embodiment of the present disclosure comprises: a first robotic arm configured to orient an imaging device; a second robotic arm configured to orient at least one surgical tool; at least one processor; and at least one memory storing instructions for execution by the at least one processor that, when executed, cause the at least one processor to: execute movements of the first robotic arm and the second robotic arm in a single coordinate system; cause the first robotic arm to position the imaging device in a location to image a region to be operated on by the surgical tool; receive a plurality of images from the imaging device and identify in the images of that region, anatomical features with which the surgical tool should avoid contact; determine a position of the imaging device and a position of the surgical tool; and cause the second robotic arm to guide the surgical tool away from the anatomical features with which the surgical tool should avoid contact.

Any of the aspects herein, wherein causing the first robotic arm to position the imaging device is based on a surgical plan.

Any of the aspects herein, wherein at least two predetermined positions for the imaging device are provided, and wherein the imaging device is adapted to acquire three-dimensional images in real-time.

Any of the aspects herein, wherein at least one position for the imaging device is one of: facing an intervertebral disc undergoing discectomy, within a vertebral foramen, or facing a lamina of a vertebra undergoing laminectomy or laminotomy.

Any of the aspects herein, wherein the memory stores additional instructions for execution by the at least one processor that, when executed, further cause the at least one processor to: cause the first robotic arm to move the imaging device in incremental steps such that sequential two-dimensional images are generated; and reconstruct three-dimensional images from the sequential two-dimensional images.

A method for monitoring a surgical procedure according to at least one embodiment of the present disclosure comprises: co-registering a coordinate system of a first robotic arm and a second robotic arm; determining a pose of an imaging device to provide real-time intraoperative imaging of a region of interest during the surgical procedure; identifying in the real-time images of the region of interest, anatomical elements from which a surgical tool should maintain a predetermined distance; and causing the second robotic arm to prevent the surgical tool from approaching the anatomical elements by less than the predetermined distance using the co-registration of the coordinate systems of the first and second robotic arms.

The details of one or more aspects of the disclosure are set forth in the accompanying drawings and the description below. Other elements, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the elements set forth above or described in detail below.

Numerous additional elements and advantages of the present invention will become apparent to those skilled in the art upon consideration of the embodiment descriptions provided hereinbelow.

BRIEF DESCRIPTION OF THE DRAWINGS

Embodiments of the present disclosure will be understood and appreciated more fully from the following detailed description, taken in conjunction with the drawings in which:

FIG. 3A is another example of a system according to at least one embodiment of the present disclosure;

FIG. 3B is another example of a system according to at least one embodiment of the present disclosure;

FIG. 3C is another example of a system according to at least one embodiment of the present disclosure;

FIG. 3D is another example of a system according to at least one embodiment of the present disclosure;

DETAILED DESCRIPTION

Figure 1:
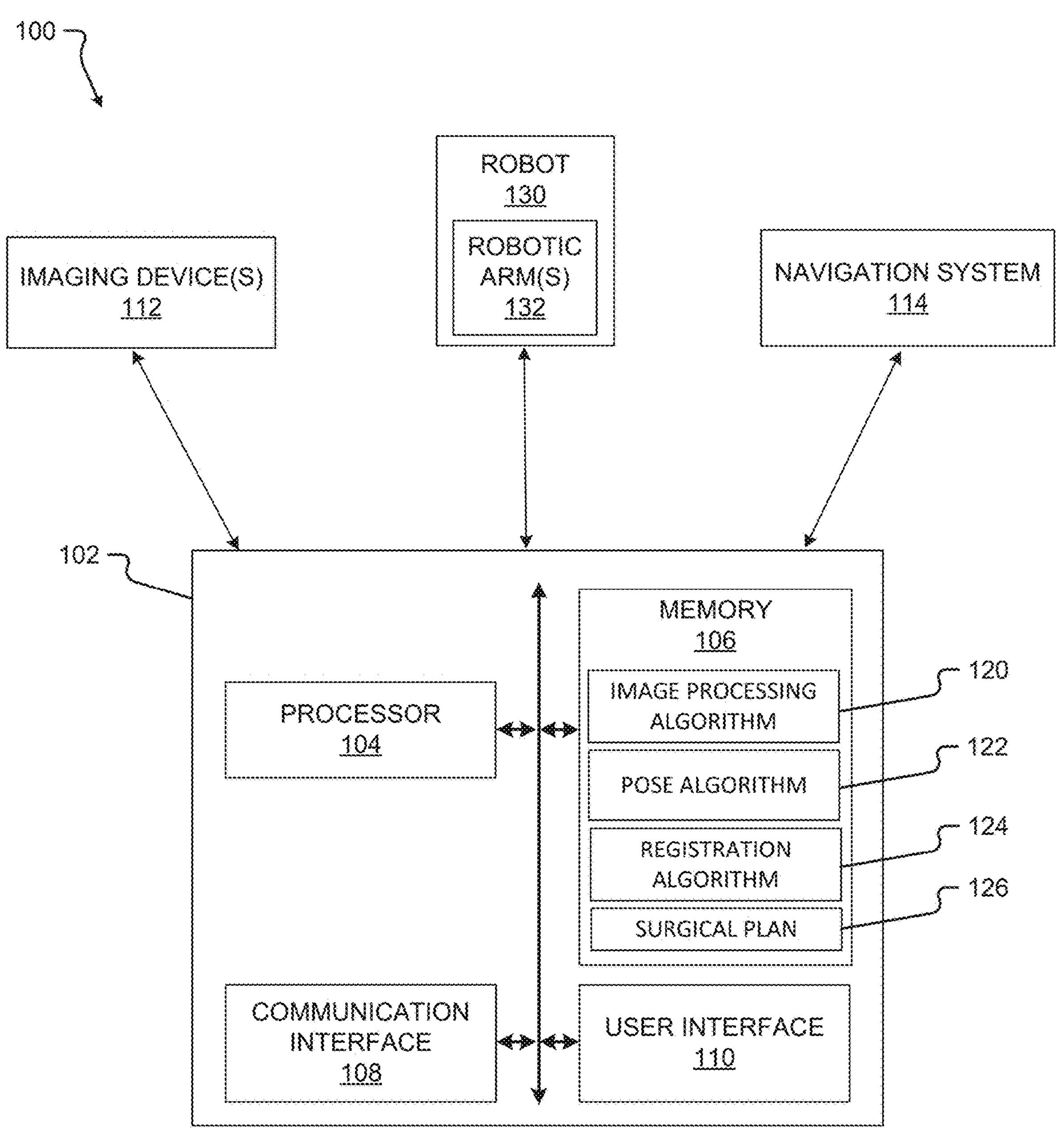
FIG. 1 shows a block diagram system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data elements and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10× Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

In many robotic surgical procedures, one or more robotic arms are registered to a preoperative image, and the image is registered to the patient's anatomy prior to a surgical procedure. However, during the course of the surgical procedure, parts of the anatomy can move relative to the main anatomical elements in the region of interest (as a result of, for example, incisions, bone osteotomies, or partial sectioning), the initial registration becomes obsolete, and updated images may be needed intraoperatively at one or more points of time during the procedure. These intraoperative images can be re-registered to the preoperative images to assist the surgeon in locating the operative area of interest. The image acquisition and registration may have limited accuracy because of potential differences in alignment, and possible inaccuracy in the registration procedure itself. Furthermore, in orthopedic spinal procedures, operations to remove small bone sections are generally either carried out without the ability of the surgeon to directly view the tissue behind or underneath the bony structure, or require a more extensive operation to provide a direct view of the region of interest. These limitations are solved by embodiments of the present disclosure.

In orthopedic procedures, especially those related to spinal surgery, the potential damage to the nervous system mandates extra care in avoiding damage to soft tissues by surgical instruments manipulated outside of the direct vision of the surgeon. It is in scenarios of indirect vision, however, that the risk of damage increases. For this reason, many operations that could be performed in a minimally invasive manner, given visualization of the underlying tissues, are currently carried out in a more invasive, open operation. Also, in spinal procedures, easily damaged and highly critical soft tissue resides in close proximity to the bony elements upon which the surgeon operates. Especially during re-operation, when a dura is adherent to perineural and peridural scar tissue, the risk of damage to the spinal meninges is high. Nerve injury, spinal fluid leak and meningitis are all possible complications of a dural tear. Thus, avoiding such complications will have beneficial effects on patient outcomes and health care costs.

During surgical procedures, visualization of soft tissue may be limited when using fluoroscopy because the procedure is time-consuming, and the accompanying radiation requires staff protection and restricts its use to intermittent images. Typically, a single C-arm machine is used, providing only two-dimensional information in a three-dimensional procedure. Thus, embodiments of the present disclosure use other imaging devices such as ultrasound or sonographic imaging, which provides high resolution soft tissue visualization and can safely be employed continuously. However, the view obtainable by a typical ultrasound probe, particularly in orthopedic procedures, is limited by bony elements impenetrable to the ultrasound field.

Robotic steering of end effectors under externally, manually-positioned ultrasound guidance has been described in the following patents and patent application publications, co-owned by the present applicant: U.S. 2017/0055940, entitled "Ultrasound guided hand held robot" and filed on Apr. 28, 2015; U.S. Pat. No. 9,420,995, entitled "Ultrasound guided robot for flexible needle steering" and filed on Jan. 27, 2014; U.S. Pat. No. 8,663,130 entitled "Ultrasound guided robot for flexible needle steering" and filed on May 31, 2009; and U.S. Pat. No. 8,571,638 entitled "Miniature bone-attached surgical robot and method of use thereof" and filed on Mar. 17, 2010, each of which is incorporated herein by reference in its entirety.

A further possible solution to increase visualization of internal tissues is the use of endoscopic probes adapted to hold and provide ultrasound imaging probes. Positioning of such probes can be accomplished using robotic guidance. Robotic positioning of endoscopic ultrasound probes has been described in An C Y et al., "An ultrasound imaging-guided robotic HIFU ablation experimental system and accuracy evaluations," Applied Bionics and Biomechanics, 2017, article ID 5868695, which is also incorporated herein by reference in its entirety.

Embodiments of the present disclosure provide new systems for a robotic system designed to improve the accuracy and safety of surgical operations on the complex bones, ligaments, and tendons of the spine. In particular, the system can be a system for spinal cord surgery and/or a spinal cord surgery system. Minimally invasive surgical procedures involving the spinal column, closely surrounding the spinal cord and nerve roots, are often performed using indirect observation of the tissue or bone being excised. The current disclosure provides methods and systems for inserting an imaging device (e.g., a miniature endoscopic ultrasound probe) into specific locations in the spinal region, from which the surgeon can view the advancement of a surgical tool in the area, and which can be used to provide information used to control the operation of the surgical tool. One exemplary system comprises at least two robotic arms, both being operated by a computing device which consequently can correlate the coordinate systems of both robotic arms. In particular, the robotic arms of the system may be controlled by a single control system. One robotic arm, hereinafter called the first robotic arm, controls a position of an imaging device such as an ultrasound probe. Another robotic arm, hereinafter called the second robotic arm, controls a position of a tool. Such small endoscopic ultrasound probes can be positioned in predefined areas and directed at specific areas of interest to provide three-dimensional (3D or 3-D) information about the tissue being treated. Safety and accuracy are enhanced because the positions of both the tool and the ultrasound probe are robotically controlled and thus known to the computing device. The computing device may also register the tool and probe with the anatomical region of interest, imaged in real-time by direct ultrasound visualization.

In at least one embodiment and using a transforaminal interbody lumbar fusion (TLIF) as an example application, during disc preparation in the initial phases of the operation, an ultrasound or other imaging probe can be placed at the edge of the annulus fibrosus in the axial plane for lateral access in annular positioning and directed at the disc space to provide warning of tool extrusion beyond the nucleus pulposus into the spinal canal. A sharp tool inadvertently entering the spinal canal could result in damage to the spinal cord of the patient. Such ultrasound probe positioning allows the surgeon to maintain a constant visualization of the surgical procedure and tool movements. The surgeon is also able to monitor the amount of disc material removed, as the computing device may be configured to compute the size and volume of the intervertebral disc on the preoperative images, and to compute the change in appearance of the disc on the intraoperative ultrasound images. In another implementation of the system, during a laminectomy or laminotomy procedure, an ultrasound or other imaging probe is placed within the vertebral foramen in the posterior disc area, and directed towards the dura to provide warning of dural damage.

In another embodiment, intraoperatively, the computing device can make concurrent adjustments in the coordinate systems of the tool and the operative field for intraoperative shifts in the anatomy resulting from procedures such as a release of vertebral lamina pressure on the spinal cord, or removal of a compressing fragment of intervertebral disc on a nerve root. Decompression of the irregular anatomical characteristics of the affected vertebrae in degenerative spine disease may result in a shift of the adjacent soft tissue, because release of pressure caused by a herniated disc or overlying bony lamina in spinal stenosis, for instance, can result in shifting positions of the soft tissue. In this situation, preoperative images may no longer be considered accurate and the surgeon is unable to rely on them. New images may therefore need to be obtained.

Calculating an optimal position and orientation for the probe to visualize the position of the tool tip in the area of interest may use an accurate 3D anatomical map that is updated in real-time to reflect the effects of the surgery. The computing device may continuously update registration of the position of the end effectors on each of the two robotic arms, both the ultrasound probe and a surgical tool, with anatomical structures in the surgical image field of view. Thus, the computing device provides three-way correlation between the ultrasound probe, the surgical tool, and the tissue upon which the procedure is being carried out. The three-way alignment in some embodiments of the present disclosure provides enhanced accuracy of the procedure.

Based on the designated surgical procedure to be performed, the computing device is programmed to select an initial optimal anatomical position (e.g., a position relative to a patient's anatomy) for an imaging device (e.g., an endoscopic ultrasound probe), to optimize the information obtained intraoperatively by the imaging device. More than one anatomical position may be selected, based on the need to visualize different areas of the anatomy during sequential phases of the operation, because of changes in the region on which the tool is operating, and based on shifts in anatomical structures as the procedure progresses, or based on the need to compute a 3-D image from multiple two-dimensional (2D or 2-D) images positioned at different angles. Intraoperatively, the computing device is configured to reposition the imaging device accordingly at every stage of the operation. Thus, as the operation proceeds, the surgeon is provided with an up-to-date virtual view, preferably unobstructed by intervening bone impenetrable to the imaging device, of the region on which the tool is working.

Embodiments of the present disclosure provide an intraoperative imaging system which overcomes at least some of the disadvantages of prior art systems and methods. Some of these limitations include the inability to visualize internal tissue elements, imaging modalities that result in exposure of the patient and staff to harmful radiation, and poor resolution of internal elements. Embodiments of the present disclosure provide new example systems for a robotic system designed to improve the accuracy and safety of surgical operations on the complex bones, ligaments, and tendons of the spine.

Embodiments of the present disclosure provide technical solutions to the problems of (1) improving tool guidance; (2) avoiding critical anatomical elements during tool movement or insertion; (3) tracking and identifying anatomical elements to avoid during surgeries; (4) posing imaging devices for tracking anatomical elements; and/or (5) increasing patient safety during robot-assisted or robotic minimally invasive surgeries.

Turning first to FIG. 1, a block diagram of a system 100 according to at least one embodiment of the present disclosure is shown. The system 100 may be used to obtain and process image data; execute one or more of the methods described herein; execute an image processing algorithm, a pose algorithm, and/or a registration algorithm; and/or carry out one or more other aspects of one or more of the methods disclosed herein. The system 100 comprises a computing device 102, one or more imaging devices 112, a navigation system 114, and/or a robot 130. Systems according to other embodiments of the present disclosure may comprise more or fewer components than the system 100. For example, the system 100 may not include the navigation system 114, or one or more components of the computing device 102.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 130, and/or the navigation system 114.

In particular, the processor 104 is configured to correlate coordinate systems of a first robotic arm and a second robotic arm. The processor 104 can also be configured to control the second robotic arm, so that the surgical tool follows an active tool path. Providing instructions to the second robotic arm to prevent the surgical tool from approaching any such identified anatomical structures by less than the predetermined distance may include updating the active tool path. This updating can be performed a real time updating based on real time imaging.

According to a further aspect, the processor 104 may be configured to calculate a feasible position of the imaging device 112 and to move the first robotic arm, so that the imaging device 112 reaches the calculated position. In particular, an ideal positioning for the robotically-controlled imaging device 112 can be determined based on the tool path and based on predetermined, acceptable positions for the imaging device 112. The calculation can be parallel to the updating of the tool path. Parallel also includes an alternating step by step calculation and/or movement of the first and second robotic arm. The active tool path can be based on a predetermined tool path.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 400, 500, 600, or 700 described herein, or of any other methods. The memory 106 may store, for example, one or more image processing algorithms 120, one or more pose algorithms 122, one or more registration algorithms 124, and/or one or more surgical plans 126. Such instructions or algorithms may, in some embodiments, be organized into one or more applications, modules, packages, layers, or engines. The algorithms and/or instructions may cause the processor 104 to manipulate data stored in the memory 106 and/or received from the imaging device 112 and/or the robot 130.

The computing device 102 may also comprise a communication interface 108. The communication interface 108 may be used for receiving image data or other information from an external source (such as the imaging device 112, the navigation system 114, and/or the robot 130), and/or for transmitting instructions, images, or other information to an external system or device (e.g., another computing device 102, the navigation system 114, the imaging device 112, and/or the robot 130). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, headset, and/or any other device for receiving information from a user and/or for providing information to a user. In some embodiments, the user interface 110 may receive information and/or commands from a user via voice activation. In other embodiments, the user interface 110 may incorporate augmented reality or virtual reality. The user interface 110 may be used, for example, to receive a user selection or other user input regarding correlating coordinate systems of a first robotic arm and a second robotic arm; to receive a user selection or other user input regarding analyzing intraoperative images obtained from an imaging device to identify anatomical elements that a surgical tool should avoid; to receive a user selection or other user input regarding preventing the surgical tool from approaching the identified anatomical elements; to receive a user selection or other user input regarding causing the second robotic arm to perform a surgical procedure using the surgical tool; to receive a user selection or other user input regarding calculating a volume of an anatomical element during the surgical procedure; and/or to receive a user selection or other user input regarding causing the first robotic arm to reposition an imaging device 112 if a region in which the surgical tool is operating becomes situated outside a field of view of the imaging device 112.

The user interface 110 may also be used, for example, to receive a user selection or other user input regarding causing the first robotic arm to reposition the imaging device 112 if any identified anatomical elements become situated outside the field of view of the imaging device 112; to receive a user selection or other user input regarding determining at least one setting of the identified imaging device 112; to receive a user selection or other user input regarding providing instructions to position and operate the surgical tool; to receive a user selection or other user input regarding modifying a surgical plan to optimize a pose of the surgical tool based on the intraoperative images; to receive a user selection or other user input regarding preventing the surgical tool from approaching an anatomical element to be avoided by at least one of preventing movement of the robotic arm supporting the surgical tool, providing an auditory, visual, tactile, or verbal alert, or disconnecting power to the tool; to receive a user selection or other user input regarding correlating the coordinate systems of the first robotic arm and the second robotic arm, such that the position of the at least one surgical tool is known in a field of view of an imaging device 112; and/or to receive a user selection or other user input regarding causing the second robotic arm to prevent the surgical tool from impinging upon the anatomical element when the intraoperative images obtained from the imaging device 112 indicate that the surgical tool is approaching at least one anatomical element to be avoided.

The user interface 110 may further be used, for example, to receive a user selection or other user input regarding executing movements of a first robotic arm and a second robotic arm in a single coordinate system; to receive a user selection or other user input regarding causing the second robotic arm to carry out the surgical procedure or operation using the at least one surgical tool; to receive a user selection or other user input regarding reconstructing three-dimensional images from the sequential two-dimensional images; to receive a user selection or other user input regarding co-registering the coordinate systems of the first and second robotic arms; to receive a user selection or other user input regarding planning the positioning of the imaging device 112 during the operative procedure to provide real-time intraoperative imaging of a region of interest; to receive a user selection or other user input regarding determining at least one setting for the imaging device 112; and/or to receive a user selection or other user input regarding identifying in the real-time images of the region of interest anatomical elements from which the surgical tool should maintain a predetermined distance.

The user interface 110 may also be used, for example, to receive a user selection or other user input regarding using the co-registration of the coordinate systems of the first and second robotic arm to cause the second robotic arm to prevent the surgical tool from approaching the anatomical elements by less than the predetermined distance; correlate the coordinate systems of the first and second robotic arms such that the positions of the imaging device and the surgical tool are mutually known; to receive a user selection or other user input regarding instructing the first robotic arm to position the imaging device in a location to image a region to be operated on by the surgical tool; to receive a user selection or other user input regarding using the imaging device to identify in images of that region, anatomical elements with which the surgical tool should avoid contact; to receive a user selection or other user input regarding using the correlated coordinate systems to determine the mutual positions of the imaging device and the surgical tool, such that the second robotic arm is instructed to guide the surgical tool away from the anatomical elements with which the surgical tool should avoid contact; and/or to receive a user selection or other user input regarding displaying instructions for moving the imaging device 112 or causing the imaging device 112 to move.

Notwithstanding the foregoing of potential uses of the user interface 110, each of the preceding inputs may be generated automatically by the system 100 (e.g., by the processor 104 or another component of the system 100) or received by the system 100 from a source external to the system 100. In some embodiments, the user interface 110 may be useful to allow a surgeon or other user to modify the instructions or other information displayed.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical element(s) (e.g., a bone, veins, tissue, etc.) and/or other patient anatomy to yield image data (e.g., image data depicting or corresponding to a bone, veins, tissue, etc.). The image data may be obtained prior to and/or during a surgical procedure and may be obtained in real-time. The imaging device 112 may be capable of taking a 2D image or a 3D image to yield the image data. "Image data" as used herein refers to the data generated or captured by an imaging device 112, including in a machine-readable form, a graphical/visual form, and in any other form. In various examples, the image data may comprise data corresponding to an anatomical element of a patient, or to a portion thereof. The imaging device 112 may be or comprise, for example, an O-arm, a C-arm, a G-arm, or any other device utilizing X-ray-based imaging (e.g., a fluoroscope, a CT scanner, or other X-ray machine); an ultrasound scanner; a magnetic resonance imaging (MRI) scanner; an optical coherence tomography scanner; an endoscope; a microscope; a thermographic camera (e.g., an infrared camera); or any other imaging device 112 suitable for obtaining images of an anatomical element of a patient.

In various implementations, wherein the imaging device 112 is an ultrasound probe, the ultrasound probe may be external or endoscopic, depending on visualization needs. In some embodiments, a transmitter (e.g., an ultrasound source) may be held by a first robotic arm and the imaging probe (e.g., an ultrasound receiver or detector) by a second robotic arm at a known distance and orientation from each other. In other embodiments, the ultrasound transmitter and the ultrasound image detector may be integrated within a single end effector.

In some implementations, the imaging device 112 and a tool may be held or otherwise supported, or oriented, by one robotic arm, or each robotic arm may hold or support, and/or orient, both an imaging device 112 and a tool. Having both the imaging device 112 and surgical tool on a single arm eliminates the potential for misalignment of two robotic arms. It will be appreciated that the description is not limited to these options; various combinations of robotic arms, imaging devices, tools, and other instruments are possible. Various implementations of the system are suitable for use in both open spinal operations and in endoscopic, transcutaneous procedures.

The navigation system 114 may provide navigation for a surgeon and/or a surgical robot during an operation. The navigation system 114 may be any now-known or future-developed navigation system, including, for example, the Medtronic StealthStation™ S8 surgical navigation system. The navigation system 114 may include a camera or other sensor(s) for tracking one or more reference markers, navigated trackers, or other objects within the operating room or other room in which some or all of the system 100 is located. In various embodiments, the navigation system 114 may be used to track a position and orientation (i.e., pose) of the imaging device 112 (or, more particularly, of a navigated tracker attached, directly or indirectly, in fixed relation to the imaging device 112). The navigation system 114 may include a display for displaying one or more images from an external source (e.g., the computing device 102, imaging device 112, or other source) or a video stream from the camera or other sensor of the navigation system 114. In some embodiments, the system 100 can operate without the use of the navigation system 114.

The robot 130 may be any surgical robot or surgical robotic system. The robot 130 may be or comprise, for example, the Mazor X™ Stealth Edition robotic guidance system. The robot 130 is configured to position the imaging device 112 at one or more precise poses and is advantageously capable of returning the imaging device 112 to the same pose(s) at a later point in time. The robot 130 may comprise one or more robotic arms 132. In some embodiments, the robotic arm 132 may comprise a first robotic arm and a second robotic arm, though the robot 130 may comprise more than two robotic arms. The first robotic arm may hold or otherwise support an imaging device 112 and the second robotic arm may hold or otherwise support another imaging device 112 or a surgical tool, and each robotic arm may be positionable independently of the other robotic arm. As a result, the first robotic arm may position the imaging device 112 independently of the pose of the second robotic arm, and the second robotic arm may position the surgical tool or another imaging device 112 independently of the pose of the first robotic arm. The imaging device 112 may be disposed on an end of the first robotic arm and/or the second robotic arm in some examples, while in other examples the imaging device 112 may be disposed on any portion of the first robotic arm, the second robotic arm, and/or the robot 130. In some embodiments, the robotic arm 132 is configured to selectively support and/or orient each of a plurality of imaging devices 112. For example, the robotic arm 132 may support and/or orient a first imaging device; remove, release, return, and/or store the first imaging device; and receive, pick up, or otherwise support a second imaging device. In some embodiments, a plurality of imaging devices 112 may be stored in a magazine or other storage unit, and the robotic arm 132 may selectively pick up and use one or more of the plurality of imaging devices 112.

The robot 130, together with the robotic arm 132, may have, for example, at least five degrees of freedom. In some embodiments the robotic arm 132 has at least six degrees of freedom. In yet other embodiments, the robotic arm 132 may have fewer than five degrees of freedom. Further, the robotic arm 132 may be positioned or positionable in any pose, plane, and/or focal point. The pose includes a position and an orientation. As a result, an imaging device 112 or other object held by the robot 130 (or, more specifically, by the robotic arm 132) may be precisely positionable in one or more needed and specific positions and orientations.

In some examples, the imaging device 112 may be an ultrasound device having an ultrasound source and an ultrasound detector, and the robotic arm 132 may comprise a first robotic arm for supporting the ultrasound source and a second robotic arm for supporting the ultrasound detector at a known distance and orientation from the ultrasound source. The robotic arm 132 may be configured to hold or support, and/or orient, an imaging device 112 and to position the imaging device 112 in a particular pose (i.e., a position and orientation). The robotic arm 132 may also be configured to move or position the imaging device 112 in various poses as calculated and/or described with respect to any one or more steps of the methods 400, 500, 600, or 700.

In some embodiments, the interoperative images obtained from the imaging device 112 are real-time images (or otherwise obtained in real-time). Real-time images are fast enough to capture the motion of the surgical tool. Real time imaging can have, for example, 20 fps or more, or 24 fps or more.

Reference markers (i.e., navigation markers) may be placed on the robot 130, the robotic arm 132, the imaging device 112, or any other object in the surgical space. The reference markers may be tracked by the navigation system 114, and the results of the tracking may be used by the robot 130 and/or by an operator of the system 100 or any component thereof. In some embodiments, the navigation system 114 can be used to track other components of the system (e.g., the imaging device 112) and the system can operate without the use of the robot 130 (e.g., with the surgeon manually manipulating the imaging device 112 and/or tool, whether based on information and/or instructions generated by the navigation system 114 or otherwise).

The system 100 or similar systems may be used, for example, to carry out one or more aspects of any of the methods 400, 500, 600, and/or 700 described herein. The system 100 or similar systems may also be used for other purposes. In some embodiments, for example, a system 100 may be used to generate a 3D model of an anatomical element or an anatomical volume of a patient. For example, the robotic arm 132 (controlled by a processor of the robot 130, the processor 104 of the computing device 102, or some other processor, with or without any manual input) may be used to position the imaging device 112 at a plurality of predetermined, known poses, so that the imaging device 112 can obtain one or more images at each of the predetermined, known poses. Because the pose from which each image is taken is known, the resulting images may be assembled together to form or reconstruct a 3D model.

Figure 2:
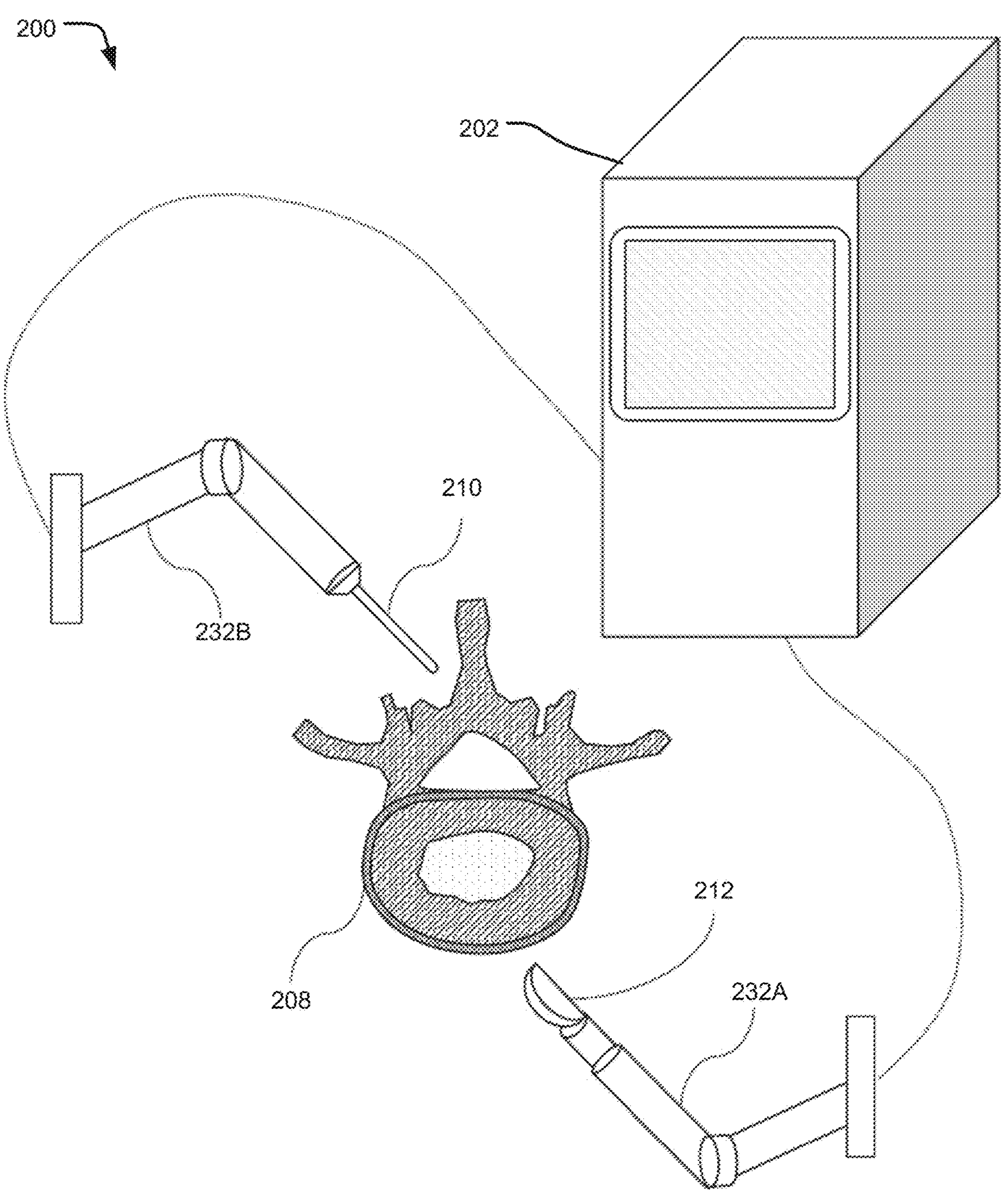
FIG. 2 is a diagram of another system according to at least one embodiment of the present disclosure.

Reference is now made to FIG. 2, which illustrates another system 200 according to at least one embodiment of the present disclosure. The system comprises at least two robotic arms 232A and 232B, which may be the same as or similar to the at least one robotic arm 132, and a computing device 202, which may be the same as or similar to the computing device 102. The computing device 202 is configured to control the pose of the robotic arms 232A, 232B. The computing device 202 may be a single unit, or may include a unit for each robot 232A, 232B, interconnected by a third computing device, but in either case, the functionality is configured such that the pose of both of the robotic arms 232A, 232B are known to each other. The first robotic arm 232A is adapted to support and/or orient an imaging device 212, which may be the same as or similar to the imaging device 112. The imaging device 212 is an ultrasound probe in some embodiments. The second robotic arm 232B is adapted to support and/or orient a surgical tool 210 to be used in the surgical procedure, such as a tool 210 that could be used for bone decompression or disc removal. In other embodiments, the first robotic arm 232A is configured to support and/or orient a transmitter of an ultrasound device and the second robotic arm 232B is configured to support and/or orient a receiver of the ultrasound device at a known distance and orientation from the first robotic arm 232A.

The system 200, and more particularly the computing device 202, may also be configured to continuously register the robotic coordinate systems of the robotic arms 232A, 232B to a surgical region of interest, by means of 2D or 3D images obtained by the imaging device 212 during a surgical procedure. The computing device 202 may perform this registration for just one of the robotic arms 232A, 232B, since the computing device 202 already relates the poses of the two arms 232A, 232B to each other. The image registration may be completed by automatically recognizing anatomical elements 208 in pre-procedural and intra-procedural images, whether by machine learning, feature or element recognition, or the like. This automatic recognition may be attained in a dual manner. First, the intrinsic characteristics of anatomical elements 208 such as bone, vessels, and nerves, that share commonalities among humans may be identified. Thus, properties such as position, size, shape, density, and signal generated in imaging studies, of the relevant elements in the region of surgical interest, may be programmed into the computing device 202. Second, the anatomical elements 208 may be identified and marked in pre-operatively acquired 3D images of the region of interest, based upon the image set used for developing a surgical plan 126. The surgical plan 126 takes into account not only the pose and action of the surgical tool 210, as moved robotically, but also the planned poses of the imaging device 212 during specific stages of the operation.

In some embodiments, the computing device 202 is configured to compare and register the images generated intraoperatively by the imaging device 212 with the surgical plan 126, either preoperatively or as amended intraoperatively, and with the known properties of the various anatomical elements 208 in the area, based on an available atlas or database of collected and averaged 3-D image sets of human spinal anatomy, or available information from a database of collected imaging studies of the area of interest in multiple human subjects. The computing device 202 may provide continual registration of the virtual representation of the operative area of interest, which may be viewable by a surgeon on a user interface 110, such as a monitor, with the actual pose of the tool 210 and the imaging device 212.

Both end effectors, namely the imaging device 212 and the tool 210, are carried by the robotic arms 232A, 232B and the positions of each robotic arm 232A, 232B are known to each other and controlled by the computing device 202. Thus, the system 200 provides for accurate control of the tool 210 positioning under real-time visualization by the images generated by the imaging device 212, since the position of each end effector is known to and controlled by the computing device 202. Moreover, the position of the anatomical elements 208 imaged by the imaging device 212 are also known to the computing device 202 and registered with the positions of the imaging device 212 and tool 210.

Thus, the three-way alignment of the tool 210, the imaging device 212, and surgical region of interest, provide a precise registration process.

Systems currently in use rely on registration of an intraoperative field of interest with preoperative 3D images. Such registration processes may have limited accuracy due to minor positioning changes between the patient at the time of the preoperative image studies and the time of the operation. By contrast, some embodiments of the present disclosure may allow precise tool alignment with an anticipated margin of error of less than 1 mm. A tool 210 supported and/or oriented by the robotic arm 232B may be used initially to inject local anesthetic for a transdermal procedure, for example, thus making use of the registration to optimize localization of the anesthetic. Specific example uses of the system 200 or 100 are provided in FIGS. 3A-D hereinbelow.

In accordance with an example surgical plan 126, the surgical tool 210 may be endoscopically viewed and positioned by identifying anatomical elements 208 and the tool 210 in images generated by the imaging device 212. The computing device 202 can then use such initial information to guide and/or optimize further surgical tool poses (e.g., position and orientation) and/or imaging device poses to ensure good visibility of the tool 210 and surrounding anatomy. Based on the surgical procedure(s) identified in the surgical plan 126, which may be generated preoperatively and modifiable intraoperatively, or based on a surgical plan 126 created intraoperatively, the computing device 202 may calculate an active tool path for the surgical tool 210. The procedure may typically be a vertebral laminectomy, laminotomy, or intravertebral disc removal, may be performed for correction of ligamentum flavum hypertrophy, bone spur removal, or may be another spinal procedure to relieve compression on a nerve root or the spinal cord.

The active tool path may be updated in real-time during the procedure by the computing device 202 or by the surgeon, based on unexpected findings during the operation, such as anatomical anomalies or unanticipated effects of the surgical procedure, or based on information obtained from images generated by the imaging device 212 intraoperatively. In particular, a change in positions of parts of a vertebral element, for example, such as resulting from the freeing of stresses by the operations executed by the tool, is a likely and common effect, which must be taken into account, since such motion may not be predictable in a surgical plan 126. The computing device 202 may program an active tool path that can be monitored by the imaging device 212 for safety and efficacy. In parallel, the computing device 202 may calculate feasible and effective imaging device 212 poses. The imaging device 212 poses may be chosen from among a limited number of preset options in which the viewing window of the imaging device 212 is directed at soft tissue in the area of the surgical manipulation. The poses are designed to provide visualization of the area of operation, both to monitor the progress of the procedure, as well as to keep sensitive elements in view during the positioning and operation of the tool 210, which is capable of causing damage to the anatomical elements 208. The imaging device 212 poses may be selected, based on the known relative positions of normal human spinal anatomy, with individual modifications for each patient. As the operation proceeds, the imaging device 212 may be automatically repositioned, either as pre-planned or according to the immediate intraoperative requirements, to enable the imaging device 212 to project a view of the region under manipulation by the surgical tool 210. The ability to provide continuous intraoperative imaging of the field of operation, and to have the surgical region of interest aligned with the tools 210 in real-time, provides an advantage over systems currently in use. Current systems may be limited by motion of the patient during the procedure, which continually makes preoperative and static intraoperative images subject to change.

Reference is now made to FIGS. 3A-D, showing positions of a tool 310 (which may be the same as or similar to the tool 210) and an imaging device 312 (which may be the same as or similar to the imaging device 112, 212) in three example applications of the system 200 (or system 100) using a posterior or lateral approach to a vertebral column 300. In all examples, the section of the vertebral column 300 undergoing operation is shown in both axial (left) and lateral (right) views. FIGS. 3A-B illustrate an example application of the system operation, using a translaminar approach for lumbar discectomy to repair a herniated nucleus pulposus of an intervertebral disc 302. During disc preparation in the initial phases of the operation, the imaging device 312 can be placed at the edge of the annulus fibrosus 304 in an axial plane, as shown in FIG. 3A, or in a vertical orientation as shown in FIG. 3B. In any orientation, the imaging device 312 is directed at the intervertebral disc 302, and moved annularly to indicate a danger of the tool 310 extrusion beyond the nucleus pulposus 316 into the adjacent bone 308, such as the end face of the vertebral body, or into a vertebral foramen (spinal canal) 314. Extrusion into the vertebral canal could result in serious damage to the patient. Such positioning of the imaging device 312 also allows the surgeon to monitor the amount of disc material removed and to maintain constant virtual visualization of the process.

FIGS. 3C-D illustrate another example use of the system 200, 100, in which a vertebra undergoing transforaminal laminectomy or laminotomy is shown in axial (left) and lateral (right) views, respectively. The positioning of the imaging device 312 in this implementation is designed to protect the neural contents 318 of the vertebral foramen 314 from intraoperative damage during opening or removal of the vertebral lamina 320, to allow access for the surgical tool 310. In this operation, the imaging device 312 can be placed within the vertebral foramen 314 in the posterior disc area and pointed toward the dura, which covers the neural elements 318, to guard against dural damage. The imaging device 312 and surgical tool 310 are viewed from above in FIG. 3C, and from an oblique lateral angle in FIG. 3D, such that in three dimensions, each object would be extending out of the plane of the drawing.

Figure 4:
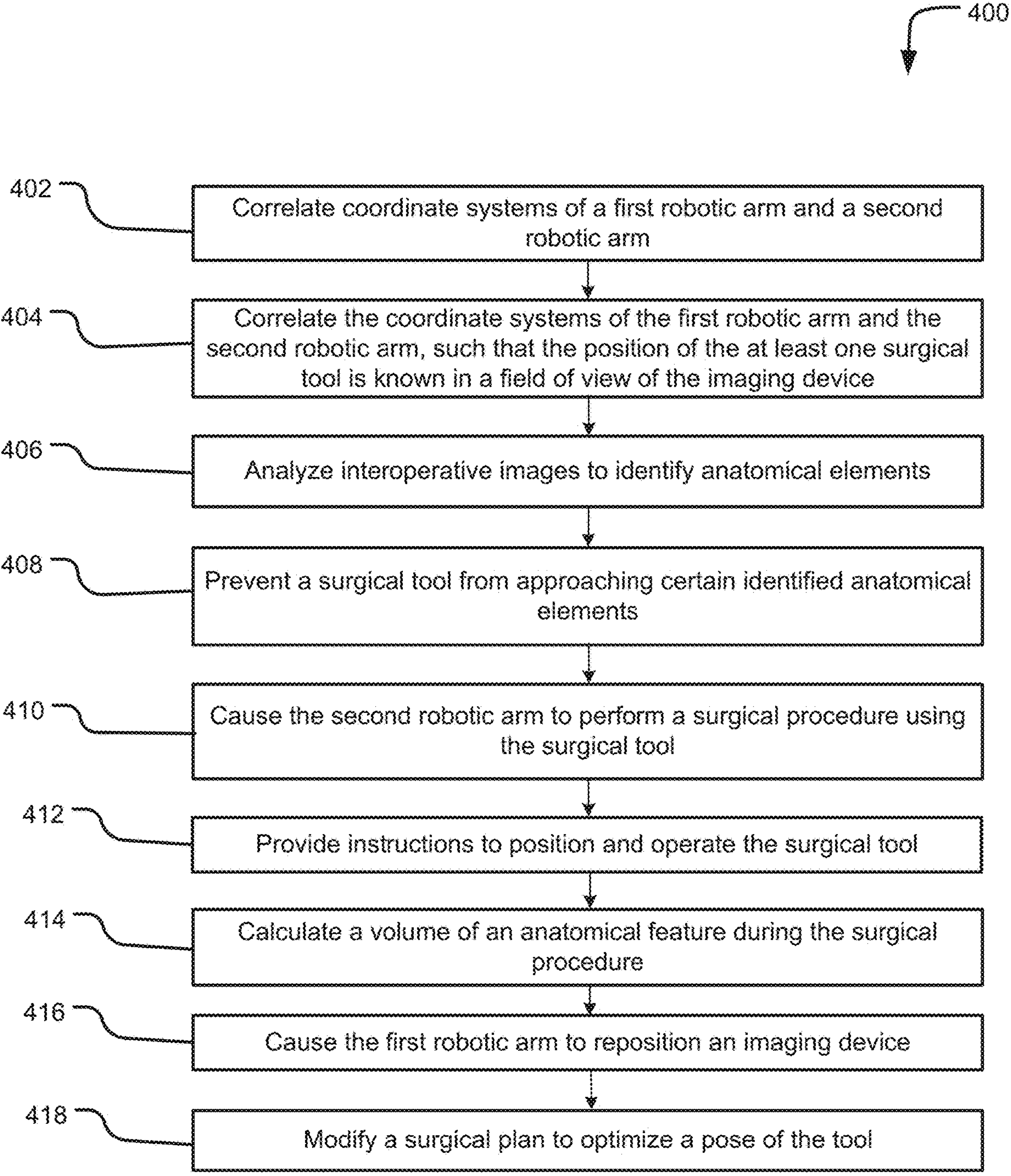
FIG. 4 is a flowchart of a method according to at least one embodiment of the present disclosure.

Turning now to FIG. 4, a method 400 for monitoring a surgical procedure according to embodiments of the present disclosure may be executed, for example, in whole or in part, on a computing device such as the computing device 102, 202 or similar device, and may utilize one or more other components of the system 100, 200 or similar components. One or more aspects of the method 400 may be performed by or with a surgical robot, a surgeon, or a combination of both using one or more imaging devices such as the imaging device 112, 212, 312.

The method 400 comprises correlating or co-registering coordinate systems of a first robotic arm, such as the robotic arm 132, 232A and a second robotic arm, such as the robotic arm 132, 232B (step 402). The correlating or co-registering may use a registration algorithm such as the registration algorithm 124. The correlating enables control of the first robotic arm and the second robotic arm in a common coordinate system so as to avoid undesired contact between the first robotic arm and the second robotic arm, and thus also to avoid undesired contact between end effectors of the first robotic arm and the second robotic arm. In some embodiments, the first robotic arm may be configured to support and/or orient the imaging device and the second robotic arm may be configured to support and/or orient a tool, such as the tool 210, 310. Though in other embodiments, the first robotic arm and/or the second robotic arm may support and/or orient any tool, instrument, or imaging device.

In some embodiments, a computing device, such as the computing device 102, 202 computes and controls a pose of the first robotic arm and a pose of the second robotic arm. The pose of each robotic arm is known to the computing device, such that the computing device correlates the poses of the first robotic arm and the second robotic arm with respect to each other, and if desired, with respect to a preoperative image or preoperative image set. Intraoperatively, the poses of the first robotic arm and the second robotic arm may be updated in real-time and recorded by the computing device, based on the images provided to the system by the imaging device during the course of the procedure. The correlation of the coordinate systems enables a surgical procedure to be carried out with a higher degree of accuracy compared to a procedure carried out in which the two robotic arms are independently operated.

The method 400 also comprises correlating coordinate systems of the first robotic arm and the second robotic arm such that a position of the tool held by the second robotic arm is known or otherwise maintained in a field of view of the imaging device held by the first robotic arm (step 404). Coordinated movement of the imaging device (via the second robotic arm) and the tool (via the first robotic arm) provides for visualization of the surgical tool position relative to the anatomical structure undergoing operation. The position of the imaging device, which is known to the computing device, and is in direct proximity to the anatomical structures in the region being treated, is updated throughout the procedure. Thus, the coordinate systems of the first robotic arm supporting and/or orienting the imaging device, the second robotic arm supporting and/or orienting the tool, and the anatomical region of surgical interest are continuously known to the computing device with a high degree of precision in real-time.

The use of two robotic arms or more working in coordination allows the imaging tool and the tool to be controlled separately, but in coordination. This allows a surgeon to keep a pose of the tool located in the anatomical field of view by means of real-time imaging, using the imaging device suitably positioned at the site of the operation. In some examples, the real-time imaging is provided by constant ultrasound monitoring of a position of relevant anatomical elements such as the anatomical element 208 (e.g., a spinal cord or nerve roots), which allows for the surgeon to have more accurate control of the procedure.

The method 400 also comprises analyzing at least one image received from the imaging device to identify anatomical elements (step 406). In some embodiments, the imaging device is an ultrasound device and the at least one image is at least one ultrasound image in which anatomical elements such as bone, vessels, nerves, a spinal nerve, a nerve root, a dorsal root ganglion, an intervertebral disc, a spinal meninges, a spinal cord, a vertebral foramen, or an intervertebral foramen, can be identified. The images may be acquired using generally available methods such as rotational scanning, slice projection, or use of integrated array transducers. The at least one image may be one or more 2-D images, one or more 3-D images, or a combination of 2-D and 3-D images. In embodiments that include 3-D images, the imaging device may be adapted to acquire 3-D images by, for example, use of at least two imaging positions of the imaging device.

The anatomical elements may be identified by executing an image processing algorithm, such as the image processing algorithm 120, with a processor such as the processor 104. The algorithm, in some embodiments, uses a neural network, machine learning, artificial intelligence, or the like, to process the image. In some embodiments, the algorithm may identify one or more anatomical elements in the image and compare them to one or more known shapes to determine whether the identified anatomical elements correlate to a known shape and can therefore be identified as a known anatomical element. In some embodiments, machine learning may be trained to recognize patterns of tissue motion during the surgical procedure, that aid in identification of specific tissues and structures. In other embodiments, the algorithm may be generated by a machine learning engine based on training data. The training data may be or comprise, for example, a plurality of images of anatomical elements that have been marked so that the machine learning engine can identify correlations between different images of the same anatomical element and thus learn to identify the anatomical element in question. For example, at least one preoperative 3-D image set, and possibly both a 3-D CT and a 3-D MRI image set, may be used to identify specific anatomical elements in a given patient to assist in planning the operation. In another example, the training data may be at least one medical database, digital surgical atlas, or other source of standardized human spine anatomy which includes the appearance of specific anatomical structures. Based on the knowledge the processor acquires from learning these image features from the training data, or based on predetermined programming, the processor has the ability to recognize and identify anatomy of specific features in any given patient.

In other embodiments, a surgeon or other user may identify the anatomical element by providing one or more inputs via a user interface such as the user interface 110. In such embodiments, the identification of the anatomical element may be based on the image and/or additional information obtained from the user.

The processor can also label or annotate specific elements in the image, which labels or annotations may identify specify areas or elements to avoid or that are forbidden to approach. For example, the processor may label one or more anatomical elements as elements to avoid by the tool. In other examples, the processor may label one or more anatomical elements as elements on which to perform a surgical procedure.

Further, the tool may be depicted in the images in real-time and poses of the tool may be obtained from the images. The tool path may thus be constantly monitored intraoperatively for safety and efficacy. The poses may also be used to guide or determine subsequent tool poses. In some embodiments, the real-time images are displayed on a user interface such as the user interface 110 for a surgeon or user to view during the procedure. The surgeon can then provide manual input to the procedure and/or monitor the procedure.

The method 400 also comprises preventing the tool from approaching certain identified anatomical element(s) (e.g., the anatomical elements previously identified to avoid) (step 408). In some embodiments, preventing the tool from approaching the anatomical element identified or labeled as an element to avoid may include preventing movement of the second robotic arm. This may include calculating or modifying an active tool path for the second robotic arm that avoids such identified elements. Modifying or calculating the active tool path may be based on a surgical plan such as the surgical plan 126. As another example a mechanical stop may be used to prevent the tool and/or the second robotic arm from approaching the identified anatomical elements. In other embodiments, preventing the tool from approaching the anatomical element identified or labeled as elements to avoid may include providing an alert to a surgeon or user. Such an alert may be visual, audible, and/or tactile. For example, an alert may be displayed on a display or provided via a headset. The alert may be audible (e.g., a beep, siren, horn, spoken warning) or visual (e.g., a flashing or illuminated light, a displayed picture or written message). In yet other embodiments, preventing the tool from approaching the identified anatomical element may include causing power to the tool to be disconnected.

The method 400 also comprises causing the second robotic arm to perform a surgical procedure using the surgical tool (step 410). Performing the surgical procedure includes positioning the surgical tool at one or more poses. The surgical procedure may be, for example, a vertebral discectomy, a laminectomy, a foraminotomy, or a laminotomy. The procedure may involve removal of all or a part of one or more of the anatomical elements identified in the step 406. In some embodiments, the surgical procedure may be or comprise removal of an intervertebral disc.

The method 400 also comprises providing instructions to position and operate the surgical tool (step 412). The instructions may comprise a surgical plan such as the surgical plan 126 for a surgical procedure and specific steps to carry out during the plan. The plan may be based on one of a set of three-dimensional preoperative images or an intraoperative plan designed by a surgeon. In some embodiments, the instructions may be instructions for the first robotic arm to position and/or operate the imaging device, or instructions for the second robotic arm to position and/or operate the tool (e.g., as described in step 410). In other embodiments, the instructions may be instructions for a surgeon or other user to position and operate the imaging device and/or the tool. In yet further embodiments, the instructions may be instructions for a surgeon or other user to position and operate the imaging device and/or the tool in conjunction with the first robotic arm and/or the second robotic arm. The instructions may be computer readable or human readable and may be outputted or transmitted to the first robotic arm, the second robotic arm, or the surgeon. The instructions may be displayed on a user interface such as the user interface 110 or in a headset, outputted audibly, or otherwise transmitted to the surgeon. The instructions may also be stored in a memory, such as the memory 106.

The method 400 also comprises calculating a volume of an anatomical feature during the surgical procedure (step 414). Calculating the volume of the anatomical feature during the surgical procedure may guide a surgeon during a procedure involving removal of all or part of an anatomical element. In instances where a known volume is to be removed, calculating the volume of the anatomical element during the procedure may inform a surgeon or a robot, such as the robot 130, of when the surgeon has removed enough material or how much material is left to remove.

The method 400 also comprises causing the first robotic arm to reposition an imaging device (step 416). In some embodiments, the imaging device is repositioned if the region in which the tool is operating becomes situated outside a field of view of the imaging device. In other words, the imaging device may be repositioned if the tool is no longer visible in image(s) obtained from the imaging device. In other embodiments, the imaging device is repositioned if any of the identified anatomical elements become situated outside the field of view of the imaging device. In other words, the imaging device may be repositioned if the identified anatomical elements are no longer visible in image(s) obtained from the imaging device. Alternatively, the imaging device may be repositioned in order to more clearly visualize the operative field in which the tool is being controlled. In another embodiment, the imaging device may be repositioned to image the identified anatomical elements, which can be used to confirm a precise location of each identified anatomical element.

The method 400 also comprises modifying a surgical plan to optimize a pose of the tool (step 418). In some embodiments, where the images received in step 406, for example, indicate that a current pose of an anatomical element on which a surgical procedure is to be performed is different than predicted, the pose of the tool may be adjusted accordingly. In other embodiments, the images received may indicate that an anatomical element to avoid is blocking or near the region of interest for the surgical procedure and that a different tool pose may better reach the desired region of interest while avoiding the anatomical element in question.

Figure 5:
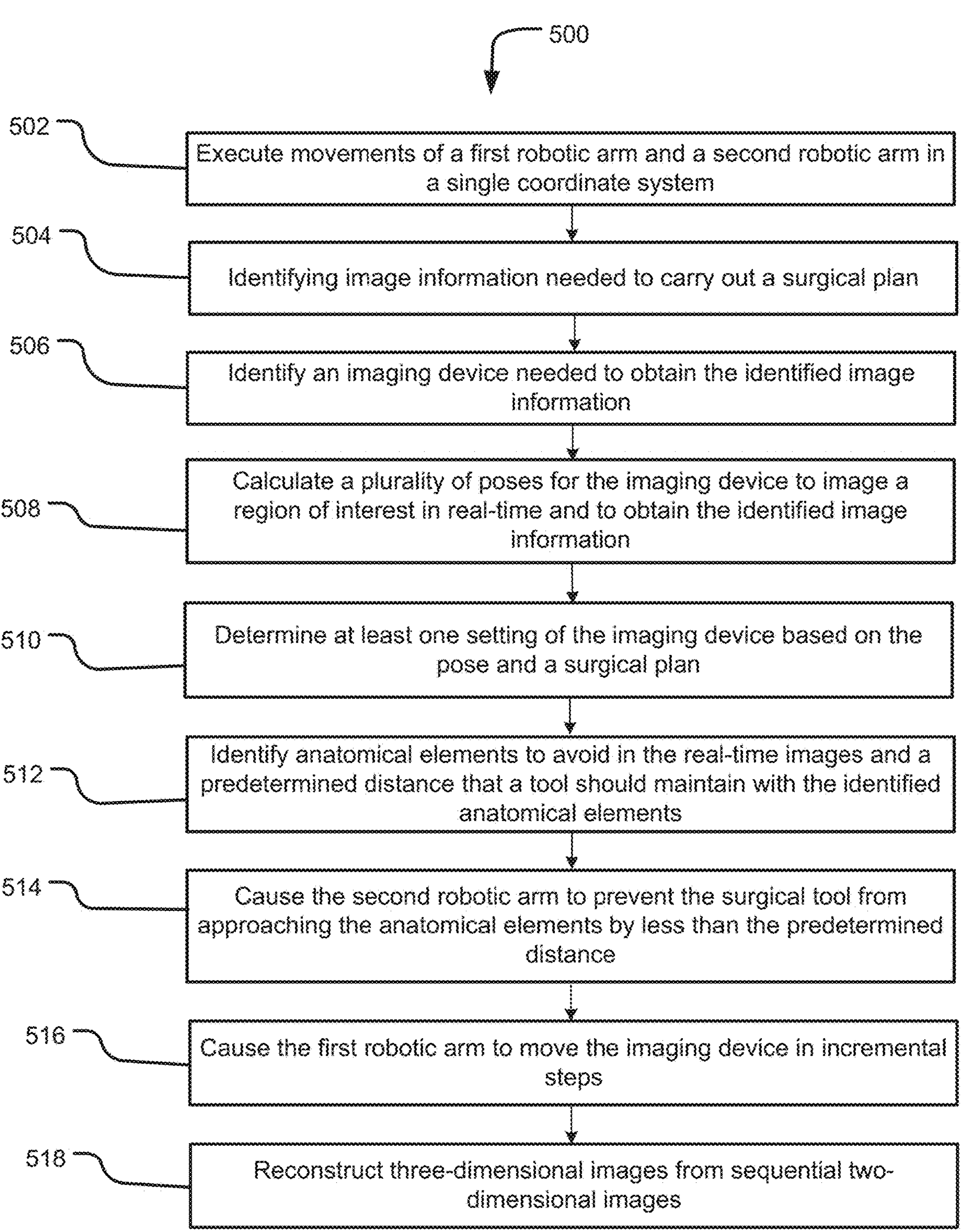
FIG. 5 is a flowchart of a method according to at least one embodiment of the present disclosure.

Turning now to FIG. 5, a method 500 for monitoring a surgical procedure according to embodiments of the present disclosure may be executed, for example, in whole or in part, on a computing device such as the computing device 102, 202 or similar device, and may utilize one or more other components of the system 100, 200 or similar components. Each step may be automatically executed by a processor such as the processor 104 of the computing device. One or more aspects of the method 500 may be performed by or with a surgical robot, a surgeon, or a combination of both using one or more imaging devices such as the imaging device 112, 212, 312.

The method 500 comprises executing movements of or otherwise controlling a first robotic arm and a second robotic arm in a single coordinate system (step 502). The first robotic arm may be, for example, a robotic arm 132, 232A. The second robotic arm may be, for example, a robotic arm 132, 232B. The coordinate system may be a robotic coordinate system, a patient coordinate system, or a navigated coordinate system.

The method 500 also comprises identifying image information needed to carry out a surgical plan (step 504). The surgical plan may be, for example, a surgical plan 126. The needed image information may be or include information about one or more anatomical features. For example, the information may be or include absolute or relative location (including location relative to one or more other anatomical features), properties and/or types of the one or more anatomical features), and/or required image depth, resolution, and/or type.

The method 500 may also comprise identifying the imaging device needed to obtain the identified image information (506). In some embodiments, the identifying may be executed automatically by a processor such as the processor 104. In other embodiments, the identifying may be performed by a surgeon or user. The imaging device (which may be, for example, an imaging device 112, 212, 312) may be selected based on the needed image information. For example, the imaging device may be selected based on whether characteristics of the imaging device enable the imaging device to obtain the identified image information. For example, one imaging device (e.g., an optical coherence tomography (OCT) camera) may be selected based on a need for detailed images of anatomical features near a surface of the anatomical tissue, and/or because imaging over a long period of time is needed (such that X-ray radiation and/or ultrasonic heating would be a concern if an X-ray imaging device or ultrasonic imaging device, respectively, were used). Another imaging device (e.g., an ultrasound probe) may be selected based on a need for images at a greater depth. The imaging device may also be selected based on dimensions of the imaging device. For example, an imaging device may be selected for its ability to fit through a small incision and/or to be used in a minimally invasive surgical system. In some embodiments, two or more imaging devices (or one imaging device with two or more configurations) may be needed to gather all of the identified imaging information. For example, an ultrasound probe may be used to gather imaging information at greater depths, and an OCT imaging device may be used to gather imaging information at shallower depths. In other embodiments, an OCT imaging device may be used for internal imaging (e.g., of an artery) while an ultrasound probe is used for external imaging.

The method 500 also comprises determining one or more poses for an imaging device to image a region of interest in real-time and obtain the identified image information (step 508). The determining may be based on the identified imaging device. In some embodiments, at least two predetermined positions for the imaging device are provided and the imaging device may be adapted to acquire 3-D images in real-time from the two predetermined positions. The one or more poses may position the imaging device at one of various positions, such as: facing an intervertebral disc undergoing discectomy; within a vertebral foramen; or facing a lamina of a vertebra undergoing laminectomy or laminotomy. The one or more poses may be selected based on anatomical constraints in normal humans, and in some implementations, based also on a set of 3-D preoperative images for a given patient. For a spinal decompression, laminectomy, or bone spur removal, the imaging device pose may position the imaging device behind or underneath bony elements to image neural tissue protected by the spinal column and provide intraoperative visualization of neural tissue that is easily damaged, and that is usually outside of the surgeon's field of vision. This positioning provides constant monitoring of the procedure being carried out by the tool held by the second robotic arm. With the inherently narrow visualization windows and multiple safety considerations of spinal operations, the system of this disclosure greatly assists the surgeon by providing a direct intraoperative view of the bone, disc, or other feature being treated and its underlying neural tissue, together with the position of the tool implementing the treatment.

The one or more poses may be determined using a pose algorithm such as the pose algorithm 122. The one or more poses may be determined based at least in part on a surgical plan such as the surgical plan 126 and/or other information about the anatomy to be imaged, so as to determine poses of the imaging device that will provide as much information as possible. This is particularly important, for example, when imaging complex bony structures, such as the spinal vertebrae, which (depending on the imaging device used) may create shadows and thus reduce the amount of information that can be gathered from an image. In embodiments where the surgical plan includes a 3D model, determining the pose may be further based on the 3D model. The one or more poses may be or include coordinates and/or an orientation of the imaging device. In some embodiments, the pose algorithm is configured to calculate the one or more poses based on the identified image information. For example, the one or more poses may be calculated based on an analysis of from which pose or positions and orientations the identified image information can be obtained. In other examples, the one or more poses may be calculated based on missing information (e.g., image data, anatomical feature properties) in a preoperative image or 3D model. In such embodiments, the one or more poses may be calculated to enable the imaging device to obtain the missing information.

In some embodiments, the one or more poses are based on the designated surgical procedure to be performed and the poses position the imaging device to optimize the information obtained intraoperatively by the imaging device. More than one anatomical position may be selected, based on the need to visualize different areas during sequential phases of the operation, because of changes in the region on which the tool is operating, and based on shifts in anatomical structures as the procedure progresses, or based on the need to compute a 3-D image from multiple 2-D images positioned at different angles. Intraoperatively, the computing device is configured to cause the first robotic arm to reposition the imaging device accordingly at every stage of the operation. Thus, as the operation proceeds, the surgeon is provided with an up-to-date virtual view, preferably unobstructed by intervening bone impenetrable to the imaging device, of the region on which the tool is working.

In other embodiments, the pose algorithm may be configured to calculate the one or more poses based on at least five degrees of freedom of movement of a robotic arm (e.g., the robotic arm 132) supporting and/or orienting the imaging device. In other embodiments, the one or more poses may be based on fewer or greater than five degrees of freedom of movement of the robotic arm. In some embodiments, the one or more poses is based on at least six degrees of freedom of movement of the robotic arm supporting and/or orienting the imaging device. Such calculations based on multiple degrees of freedom of movement advantageously enable calculations of precise poses in planes and/or focal points that may not be obtainable by imaging devices without use of a robotic arm.

In yet other embodiments, the pose algorithm may be configured to calculate the one or more poses based on input or feedback from the surgeon or operator. For example, the surgeon or operator may wish to obtain an image of an anatomical feature from a certain angle or plurality of angles. In another example, the surgeon may wish to non-invasively position the imaging device, while in other examples the surgeon may wish to invasively position the imaging device.

The method 500 also comprises determining at least one setting of the imaging device based on the pose and a surgical plan (step 510). In some embodiments, the determining may be executed automatically by a processor such as the processor 104. In other embodiments, the determining may be performed by a surgeon or user. The at least one setting includes, but is not limited to, resolution, depth, type, and/or imaging duration. Determining the at least one setting may be based on at least one characteristic of the imaging device and/or the surgical plan. The at least one setting may also be based on the poses determined in step 508 as described above. The at least one setting may also be based on the identified image information and/or the pose. For example, for a given image to be taken with an ultrasound probe at a certain pose, a long depth of penetration may be preferable to a high resolution, while for another image, the opposite may be true. In some embodiments, the at least one setting is based on input or feedback from the surgeon or operator. For example, the surgeon or operator may wish to obtain an image of an anatomical feature from a certain angle. The at least one setting may be different for each imaging device of a plurality of imaging devices that will be used to obtain the needed image information. In some embodiments, the at least one setting of one imaging device may be different for each image to be taken with the one imaging device, so as to obtain images with varying information. In other embodiments, the at least one setting may be determined during a calibration process.

The method 500 also comprises identifying, in real-time images obtained from the imaging device at the pose using the at least one setting, one or more anatomical element from which the surgical tool should maintain a predetermined distance (step 512). The one or more anatomical elements may be, for example, an anatomical element 208. Identifying the anatomical elements may be the same as or substantially similar to the step 406 of the method 400 described above. Additionally, the predetermined distance may be determined from the images and/or a surgical plan such as the surgical plan 126. The predetermined distance may prevent the tool from affecting or otherwise contacting the anatomical elements to avoid while also obtaining a desired path to a region of interest or anatomical element. In some embodiments, the predetermined distance may be an input received at a user interface (such as the user interface 110) or received from the surgical plan. In other embodiments, a processor such as the processor 104 may calculate the predetermined distance and/or a position in the real-time images into a real position. In particular, the processor can be configured to calculate a distance between an identified anatomical structure from which the surgical tool should maintain a predetermined distance and the surgical tool; and further to calculate a corresponding real distance of between an identified anatomical structure from which the surgical tool should maintain a predetermined distance and the surgical tool.

The method 500 also comprises causing the second robotic arm to prevent the tool from approaching the anatomical element(s) identified in step 510 by less than the predetermined distance identified in step 512 (step 514). This step may include calculating or modifying an active tool path to maintain at least the predetermined distance between the tool and the identified anatomical elements. Adjustment of the active tool path may be carried out, e.g., by knowledge of the position of the tool relative to forbidden objects in the operative field, as described in U.S. Patent Application Publication No. 2012/0143084, entitled "Device for improving the accuracy of manual operations" and filed on Aug. 17, 2010, which is incorporated herein by reference in its entirety. Another example for preventing the tool from approaching the identified anatomical elements by controlling the second robotic arm may include positioning a mechanical stop at the predetermined distance to prevent the tool and/or the second robotic arm from approaching to within less than the predetermined distance of the identified anatomical elements.

The method 500 also comprises causing the first robotic arm to move the imaging device in incremental steps such that sequential 2-D images are generated (step 516). A position of the imaging device at each incremental step may be based on a surgical plan such as the surgical plan 126. In some embodiments, a single imaging device may be used to obtain the sequential 2-D images. In other embodiments, a plurality of imaging devices held by a plurality of robotic arms may be used to obtain the sequential 2-D images. Alternatively, a plurality of robotic arms may support and/or orient a plurality of types of imaging devices (e.g., one robotic arm may support and/or orient an imaging device configured to image hard tissue, and another robotic arm may support and/or orient an imaging device configured to image soft tissue), so that more information (e.g., information about both hard and soft tissue) may be included in the 3D model.

The method 500 also comprises reconstructing 3-D images from sequential 2-D images (step 518). The sequential 2-D images may be images obtained during the step 516 in some embodiments. In other words, to reconstruct the 3-D images, the first robotic arm may be configured to move the imaging device in incremental steps such that sequential 2-D images are generated as described in step 516. In other embodiments, the sequential 2-D images may be received from a communication interface such as the communication interface 108.

The sequential 2-D images may then be used to reconstruct the 3-D images. Reconstructing, in some embodiments, includes updating a 3-D model with updated information obtained from the sequential 2-D images. Reconstructing, in other embodiments, includes generating a new 3-D model based on the sequential 2-D images. Updating or newly generating a 3D model of a relevant portion of a patient's anatomy in this manner beneficially yields a model that reflects changes resulting from the surgical procedure. For example, if one or more anatomical features have shifted during the procedure (whether as a result of the procedure itself or for any other reason), then the reconstruction may be used to update or newly generate a 3D model before continuing with the procedure. As another example, if one or more anatomical features have been changed by the procedure (e.g., by the removal of bony or soft tissue or otherwise), then the reconstruction may be used to update or newly generate a 3D model to reflect the change.

Figure 6:
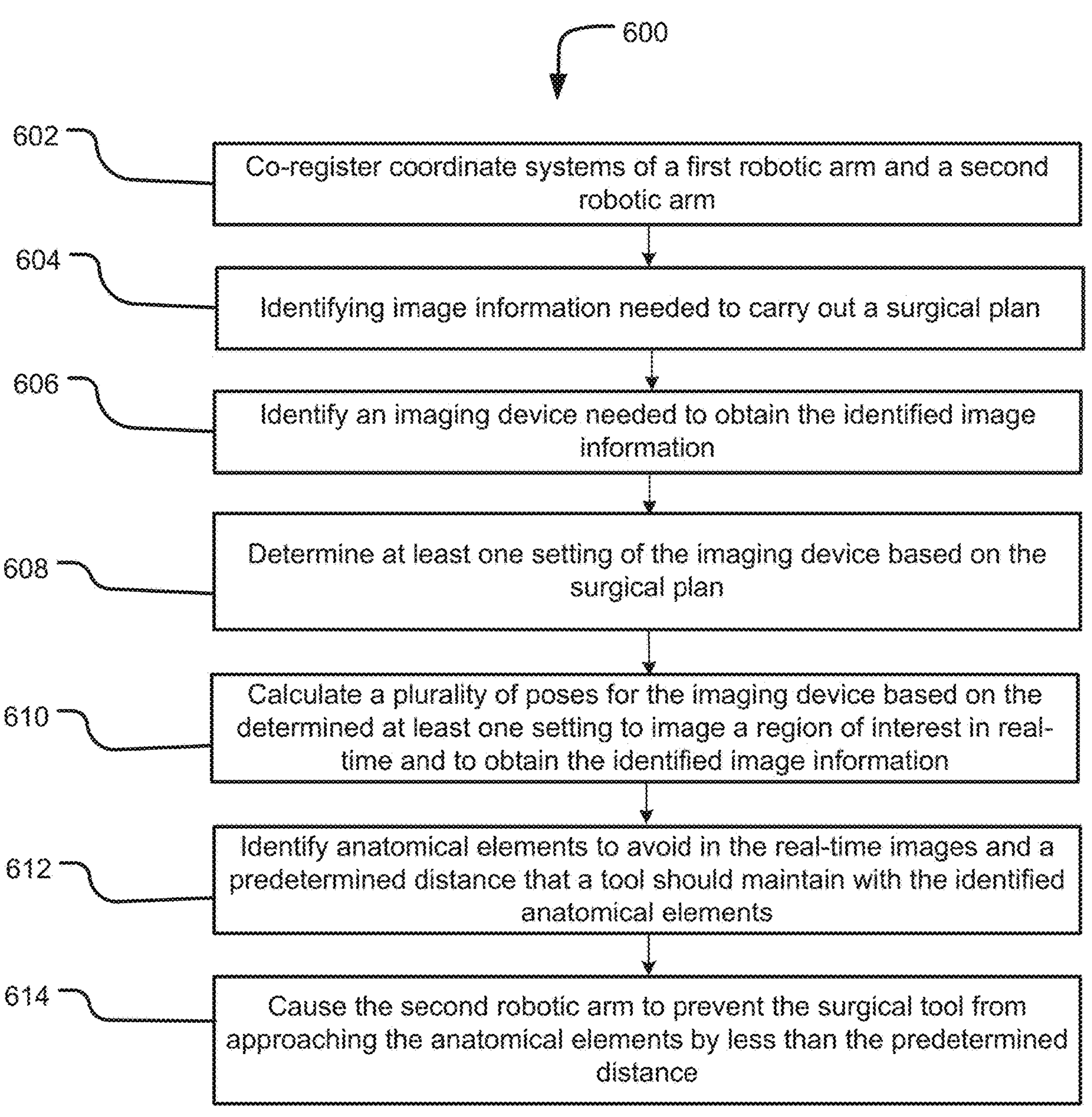
FIG. 6 is a flowchart of a method according to at least one embodiment of the present disclosure.

Turning now to FIG. 6, a method 600 for monitoring a surgical procedure according to embodiments of the present disclosure may be executed, for example, in whole or in part, on a computing device such as the computing device 102, 202 or a similar device, and may utilize one or more other components of the system 100, 200 or similar components. Each step may be automatically executed by a processor such as the processor 104 of the computing device 102, 202. One or more aspects of the method 600 may be performed by or with a surgical robot, a surgeon, or a combination of both using one or more imaging devices such as the imaging device 112, 212, 312.

The method 600 comprises co-registering coordinate systems of a first robotic arm and a second robotic arm (step 602). The first robotic arm and the second robotic arm may be the same as or similar to the robotics 232A, 232B described above, or any other robotic arm described herein. In some embodiments, the step 602 is the same as the step 402 of the method 400 described above. In other embodiments, the step 602 is similar to the step 402 of the method 400 described above.

The method 600 also comprises identifying image information needed to carry out a surgical plan (step 604). The surgical plan may be the same as or similar to the surgical plan 126. In some embodiments, the step 604 is the same as the step 504 of the method 500 described above. In other embodiments, the step 604 is similar to the step 504 of the method 500 described above.

The method 600 may also comprise identifying the imaging device needed to obtain the identified image information (606). In some embodiments, the step 606 is the same as the step 506 of the method 500 described above. In other embodiments, the step 606 is similar to the step 506 of the method 500 described above. Further, in some embodiments, the identifying may be executed automatically by a processor such as the processor 104. In other embodiments, the identifying may be performed by a surgeon or user.

The method 600 also comprises determining at least one setting for the imaging device (step 608). In some embodiments, the determining may be executed automatically by a processor such as the processor 104. In other embodiments, the determining may be performed by a surgeon or user. The at least one setting may be determined based on a surgical plan such as the surgical plan 126. The at least one setting may include, but is not limited to, resolution, depth, type, and/or imaging duration. The at least one setting may be determined based on at least one characteristic of the imaging device and/or the surgical plan. The at least one setting may also be based on (or may be determined based on) image information needed by the surgeon or called for in a surgical plan. For example, for a given image to be taken with an ultrasound probe at a certain pose, a long depth of penetration may be preferable to a high resolution, while for another image, the opposite may be true. In some embodiments, the at least one setting is based on input or feedback from the surgeon or operator. For example, the surgeon or operator may wish to obtain an image of an anatomical feature from a certain angle. The at least one setting may be different for each imaging device of a plurality of imaging devices that will be used to obtain the needed image information. In some embodiments, the at least one setting of one imaging device may be different for each image to be taken with any one imaging device, so as to obtain images with varying information. In other embodiments, the at least one setting may be determined during a calibration process.

The method 600 also comprises determining one or more poses for an imaging device to image a region of interest in real-time based on the at least one setting (step 610). The step 610 may be the same as or similar to the step 508 of the method 500 described above. Additionally, the pose algorithm may be configured to calculate the one or more poses based on one or more characteristics of the imaging device settings determined in the step 608 (e.g., resolution, image type, image dimension, shutter speed, device dimensions, image depth, etc.). For example, if the area to be imaged includes bony tissue, and the imaging device is an ultrasound probe, then the one or more poses may be calculated to avoid "shadows" caused by the inability of ultrasound waves to penetrate the bony tissue. More specifically, the one or more poses may be selected, for example, to obtain image data from two different trajectories on different sides of the bony tissue, so that portions of the imaged area that are in a "shadow" in one image are clearly shown in the other, and vice versa. Alternatively, if information is needed only about the anatomy on one side of the bony tissue, one or more poses may be calculated that will ensure the area of interest is not in a "shadow" of the bony tissue. The poses may also be calculated based at least in part on a preoperative image or 3D model that forms part of a surgical plan. In some such embodiments, the preoperative image or the 3D model may be utilized to facilitate calculation of poses that will enable needed information to be obtained in a more efficient manner than might otherwise be possible.

The method 600 also comprises identifying, in real-time images obtained from the imaging device at the pose using the at least one setting, one or more anatomical element(s) from which the surgical tool should maintain a predetermined distance (step 612). The one or more anatomical elements may be or include, for example, an anatomical element such as the anatomical element 208. In some embodiments, the step 612 is the same as the step 512 of the method 500 described above. In other embodiments, the step 624 is similar to the step 512 of the method 500 described above.

The method 600 also comprises causing the second robotic arm to prevent a surgical tool from approaching the anatomical elements by less than the predetermined distance determined in step 608 (step 614). In some embodiments, the step 614 is the same as the step 514 of the method 500 described above. In other embodiments, the step 614 is similar to the step 514 of the method 500 described above.

Figure 7:
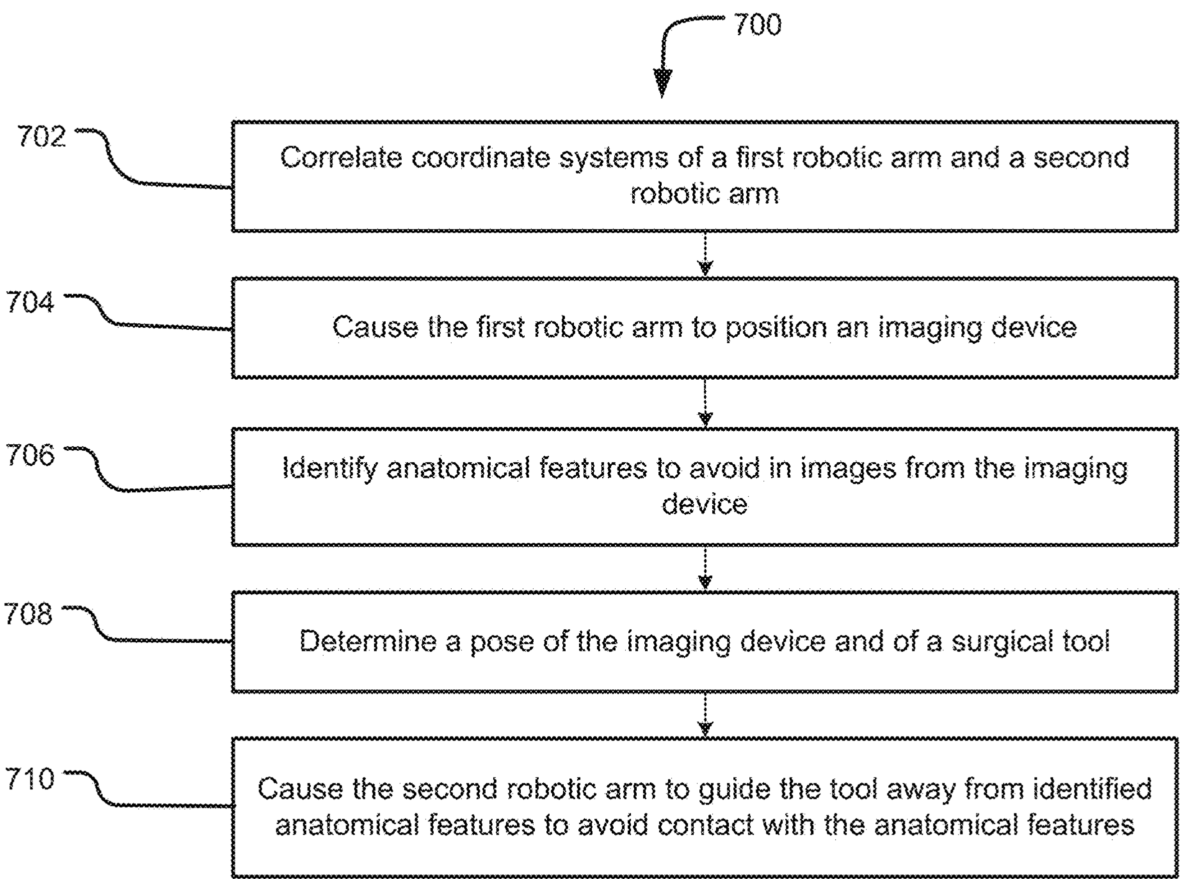
FIG. 7 is a flowchart of a method according to at least one embodiment of the present disclosure.

Turning now to FIG. 7, a method 700 for monitoring a surgical procedure according to embodiments of the present disclosure may be executed, for example, in whole or in part, on a computing device such as the computing device 102, 202 or a similar device, and may utilize one or more other components of the system 100, 200 or similar components. One or more aspects of the method 700 may be performed by or with a surgical robot, a surgeon, or a combination of both using one or more imaging devices such as the imaging device 112, 212, 312.

The method 700 comprises co-registering a coordinate system of a first robotic arm and a second robotic arm (step 702). In some embodiments, the step 702 is the same as the step 402 of the method 400 described above. In other embodiments, the step 702 is similar to the step 402 of the method 400 described above.

The method 700 also comprises causing the first robotic arm to position the imaging device (step 704). The imaging device may be positioned internal and/or external to the patient. The imaging device may be positioned according to a surgical plan such as the surgical plan 126. As previously described, internal imaging devices may include, but are not limited to, an endoscope, a probe, or a microscope, and external imaging devices may include, but are not limited to, an ultrasound probe, an X-ray imaging device, or a CT scanner. In some embodiments, one imaging device 112 may be used during the procedure. In other embodiments, two or more imaging devices may be used during the procedure. When two or more imaging devices are used, a first one or more imaging devices may be used internally and a second one or more imaging devices may be used externally, though in other examples each of the two or more imaging devices may be used internally or externally.

The method 700 also comprises identifying anatomical features to avoid in one or more images obtained from the imaging device (step 706). In some embodiments, the step 706 is the same as the step 404 of the method 400 described above. In other embodiments, the step 706 is similar to the step 404 of the method 400 described above.

The method 700 also comprises determining a pose of the imaging device and of a surgical tool (step 708). The surgical tool may be, for example, a tool 210, 310. The poses of the imaging device and of the surgical tool may be determined from or using the correlated coordinate system. The poses of the imaging device and of the surgical tool also may be determined from pose information received from the first robotic arm and the second robotic arm, respectively. The pose information may include both positional data and orientation data. In some embodiments, the pose information may be received from one or more sensors disposed on or integrated with the first robotic arm and the second robotic arm. In other embodiments, the pose information may be received from a navigation system such as the navigation system 114. The pose of the imaging device may be determined based on the anatomical features to avoid identified in step 706. The imaging device may be posed so as to image the anatomical feature to avoid, which may be used to confirm a precise location of each anatomical feature to avoid.

The method 700 also comprises causing the second robotic arm to guide the tool away from the one or more anatomical features identified in the step to avoid contact with those one or more anatomical features (step 710). The one or more anatomical features may be or include an anatomical element such as the anatomical element 208. The step 710 may include calculating or modifying an active tool path to avoid such identified features and/or to guide the tool away from the one or more anatomical features. Another example may include using a mechanical stop to prevent the second robotic arm from approaching the identified anatomical elements. In some embodiments, the mechanical stop may cause the second robotic arm to deflect or move away from the one or more anatomical features.

Other example uses of the systems 100, 200 and the methods 400, 500, 600, and 700 are possible. For example, the systems and methods disclosed herein may be applied to other areas of the nervous system in which visualization of a soft tissue (such as the spinal cord, nerve roots, the optic globe, or intracerebral tissue) is impeded by ultrasound-impenetrable or ultrasound-dense elements such as bone. In some examples, by inserting an endoscopic ultrasound probe beyond the surface of the hard element, visualization of the area of interest may be obtained. The system may be used for intracerebral operations, such as tumor removal by endoscopic guidance, in areas in which direct visualization is impossible or impractical. Tumors of the pituitary, cochlear nerve, or other non-brain tissue in the head and neck area are candidates for removal using the embodiments of the present disclosure as well.

In various example applications, an ultrasound probe may be external, as visualization needs require. Multiple ultrasound probes and additional robotic arms may be incorporated. The robotic arms may be adapted to carry other medical equipment or devices, including, for example, imaging devices, pressure gauges, or other devices for quantitative measurements. An ultrasound transmitter may be held by one robotic arm and the ultrasound imager by a second arm. Other imaging techniques such as optical imaging may also be incorporated in addition or as an alternative to ultrasound imaging. In some implementations, the robotic arm may be used to move the ultrasound probe systematically in incremental steps to allow for 3-D spatial reconstruction of sequential 2-D images. The ability to visualize the tissue in three dimensions provides the surgeon with depth perception of the operating field, further improving safety and accuracy.

As may be appreciated based on the foregoing disclosure, the present disclosure encompasses methods with fewer than all of the steps identified in FIGS. 4, 5, 6, and 7 (and the corresponding description of the methods 400, 500, 600, and 700), methods that include additional steps beyond those identified in FIGS. 4, 5, 6, and 7 (and the corresponding description of the methods 400, 500, 600, and 700), and methods with one or more different steps than those identified in FIGS. 4, 5, 6, and 7 (and the corresponding description of the methods 400, 500, 600, and 700).

The foregoing discussion has been presented for purposes of illustration and description. The foregoing is not intended to limit the disclosure to the form or forms disclosed herein. In the foregoing Detailed Description, for example, various elements of the disclosure are grouped together in one or more aspects, embodiments, and/or configurations for the purpose of streamlining the disclosure. The elements of the aspects, embodiments, and/or configurations of the disclosure may be combined in alternate aspects, embodiments, and/or configurations other than those discussed above. This method of disclosure is not to be interpreted as reflecting an intention that the claims require more elements than are expressly recited in each claim. Rather, as the following claims reflect, inventive aspects lie in less than all elements of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A robotic system, comprising:

a first robotic arm configured to orient an imaging device;

a second robotic arm configured to orient a surgical tool;

a processor; and a memory storing instructions for execution by the processor that, when executed, enable the processor to:

annotate a plurality of intraoperative images obtained from the imaging device to label a first anatomical element for the surgical tool to avoid;

prevent the surgical tool from approaching the first anatomical element;

calculate, based on the plurality of intraoperative images, a volume of a second anatomical element;

remove an amount of material from the second anatomical element;

recalculate the volume of the second anatomical element to determine the amount of material removed; and generate a notification when the determined amount of material removed equals or is greater than a known volume to be removed.

2. The robotic system of claim 1, wherein the memory stores additional instructions for execution by the processor that, when executed, further enable the processor to:

obtain a pose of the surgical tool.

3. The robotic system of claim 2, wherein the memory stores additional instructions for execution by the processor that, when executed, further enable the processor to:

cause the second robotic arm to perform a surgical procedure using the surgical tool.

4. The robotic system of claim 3, wherein the surgical procedure comprises a vertebral discectomy, a laminectomy, a foraminotomy, or a laminotomy.

5. The robotic system of claim 1, wherein the memory stores additional instructions for execution by the processor that, when executed, further enable the processor to:

analyze the plurality of intraoperative images to identify the first anatomical element.

6. The robotic system of claim 5, wherein identifying the first anatomical element is accomplished through image processing or through machine learning recognition of images of anatomical elements from a database.

7. The robotic system of claim 1, wherein the memory stores additional instructions for execution by the processor that, when executed, further enable the processor to:

cause the first robotic arm to reposition the imaging device if the first anatomical element becomes situated outside a field of view of the imaging device.

8. The robotic system of claim 1, wherein the first anatomical element comprises a spinal nerve, a nerve root, a dorsal root ganglion, an intervertebral disc, a spinal meninges, a spinal cord, a vertebral foramen, or an intervertebral foramen.

9. The robotic system of claim 1, wherein the memory stores additional instructions for execution by the processor that, when executed, further enable the processor to:

provide information for positioning and operating the surgical tool.

10. The robotic system of claim 9, wherein the information comprises a plan for a surgical procedure based on an intraoperative plan designed by a surgeon.

11. The robotic system of claim 10, wherein the memory stores additional instructions for execution by the processor that, when executed, further enable the processor to:

modify the intraoperative plan to optimize a pose of the surgical tool based on images received from the imaging device.

12. A system, comprising:

a robotic arm configured to orient an imaging device;

a processor; and a memory storing instructions for execution by the processor that, when executed, enable the processor to:

annotate a plurality of intraoperative images obtained from the imaging device to label a first anatomical element for a surgical tool to avoid;

prevent the surgical tool from approaching the first anatomical element;

calculate, based on the plurality of intraoperative images, a volume of a second anatomical element;

remove an amount of material from the second anatomical element;

recalculate the volume of the second anatomical element to determine the amount of material removed; and generate a notification when the determined amount of material removed equals or is greater than a known volume to be removed.

13. The system of claim 12, wherein the surgical tool is oriented by a second robotic arm.

14. The system of claim 13, wherein the memory stores additional instructions for execution by the processor that, when executed, further enable the processor to:

cause the second robotic arm to perform a surgical procedure using the surgical tool.

15. The system of claim 13, wherein the memory stores additional instructions for execution by the processor that, when executed, further enable the processor to:

obtain a pose of the surgical tool.

16. The system of claim 12, wherein the memory stores additional instructions for execution by the processor that, when executed, further enable the processor to:

cause the robotic arm to position the imaging device based on a surgical plan.

17. The system of claim 12, wherein at least two predetermined positions for the imaging device are provided, and wherein the imaging device is adapted to acquire three-dimensional images in real-time.

18. The system of claim 17, wherein at least one position of the at least two predetermined positions comprises one of: facing an intervertebral disc undergoing discectomy, within a vertebral foramen, or facing a lamina of a vertebra undergoing laminectomy or laminotomy.

19. The system of claim 12, wherein the memory stores additional instructions for execution by the processor that, when executed, further enable the processor to:

cause the robotic arm to move the imaging device in incremental steps to generate two-dimensional images; and reconstruct at least one three-dimensional image from the two-dimensional images.

20. A method, comprising:

annotating a plurality of intraoperative images obtained from an imaging device to label a first anatomical element for a surgical tool to avoid;

preventing the surgical tool from approaching the first anatomical element;

calculating, based on the plurality of intraoperative images, a volume of a second anatomical element;

removing an amount of material from the second anatomical element;

recalculating the volume of the second anatomical element to determine the amount of material removed; and generating a notification when the determined amount of material removed equals or is greater than a known volume to be removed.

* * * * *